(12) United States Patent
Flaherty et al.

(10) Patent No.: US 8,560,041 B2
(45) Date of Patent: Oct. 15, 2013

(54) BIOLOGICAL INTERFACE SYSTEM

(75) Inventors: J. Christopher Flaherty, Topsfield, MA (US); Richard A. Van Wagenen, Salt Lake City, UT (US); Christopher Smith, Salt Lake City, UT (US); Christine Decaria, Salt Lake City, UT (US); Almut Branner, Salt Lake City, UT (US); Nephi Harvey, Kayesville, UT (US)

(73) Assignee: BrainGate Co., LLC, Ponte Vedra Beach, FL (US)

( * ) Notice: Subject to any disclaimer, the term of this patent is extended or adjusted under 35 U.S.C. 154(b) by 2414 days.

(21) Appl. No.: 11/240,652

(22) Filed: Oct. 3, 2005

(65) Prior Publication Data

US 2006/0173259 A1  Aug. 3, 2006

Related U.S. Application Data

(60) Provisional application No. 60/615,629, filed on Oct. 4, 2004.

(51) Int. Cl.
*A61B 5/00* (2006.01)

(52) U.S. Cl.
USPC .................. 600/373; 600/372; 601/1; 601/2; 601/115; 601/116

(58) Field of Classification Search
None
See application file for complete search history.

(56) References Cited

U.S. PATENT DOCUMENTS

| | | | |
|---|---|---|---|
| 3,837,339 A | 9/1974 | Aisenberg et al. | |
| 3,850,161 A | 11/1974 | Liss | |
| 4,055,175 A | 10/1977 | Clemens et al. | |
| 4,146,029 A | 3/1979 | Ellinwood, Jr. | |
| 4,294,245 A | 10/1981 | Bussey | |
| 4,360,031 A | 11/1982 | White | |
| 4,461,304 A | 7/1984 | Kuperstein | |
| 4,524,774 A | 6/1985 | Hildebrandt et al. | |
| 4,566,464 A | 1/1986 | Piccone et al. | |
| 4,569,352 A | 2/1986 | Petrofsky et al. | |
| 4,633,889 A | 1/1987 | Talalla et al. | |
| 4,690,142 A | 9/1987 | Ross et al. | |

(Continued)

FOREIGN PATENT DOCUMENTS

EP    0 911 061 A    4/1999
WO    WO 01/43635    6/2001

(Continued)

OTHER PUBLICATIONS

Touradj Ebrahimi et al., Brain-computer Interface in Multimedia Communication, IEEE Signal Processing Magazine, vol. 20, No. 1, Jan. 2003, pp. 14-24.

(Continued)

*Primary Examiner* — Christopher D Koharski
*Assistant Examiner* — Deborah Malamud
(74) *Attorney, Agent, or Firm* — SoCal IP Law Group LLP; M. Kala Sarvaiya; Steven C. Sereboff

(57) ABSTRACT

A system and method for an improved biological interface system that processes multicellular signals of a patient and controls one or more devices is disclosed. The system includes a sensor that detects the multicellular signals and a processing unit for producing the control signal based on the multicellular signals. The system may include improved communication, self-diagnostics, and surgical insertion tools.

115 Claims, 11 Drawing Sheets

(56) References Cited

U.S. PATENT DOCUMENTS

| | | |
|---|---|---|
| 4,837,049 A | 6/1989 | Byers et al. |
| 4,865,048 A | 9/1989 | Eckerson |
| 4,878,913 A | 11/1989 | Aebischer et al. |
| 4,883,666 A | 11/1989 | Sabel et al. |
| 4,969,468 A | 11/1990 | Byers et al. |
| 5,037,376 A | 8/1991 | Richmond et al. |
| 5,081,990 A | 1/1992 | Deletis |
| 5,092,329 A | 3/1992 | Graupe et al. |
| 5,112,296 A | 5/1992 | Beard et al. |
| 5,119,832 A | 6/1992 | Xavier |
| 5,156,844 A | 10/1992 | Aebischer et al. |
| 5,215,088 A | 6/1993 | Normann et al. |
| 5,325,862 A | 7/1994 | Lewis et al. |
| 5,325,865 A | 7/1994 | Beckman et al. |
| 5,361,760 A | 11/1994 | Normann et al. |
| 5,413,611 A | 5/1995 | Haslam et al. |
| 5,423,877 A | 6/1995 | Mackey |
| 5,445,608 A | 8/1995 | Chen et al. |
| 5,458,631 A | 10/1995 | Xavier |
| 5,474,082 A | 12/1995 | Junker |
| 5,474,547 A | 12/1995 | Aebischer et al. |
| 5,549,656 A | 8/1996 | Reiss |
| 5,617,871 A | 4/1997 | Burrows |
| 5,638,826 A | 6/1997 | Wolpaw et al. |
| 5,687,291 A | 11/1997 | Smyth |
| 5,692,517 A | 12/1997 | Junker |
| 5,697,951 A | 12/1997 | Harpstead et al. |
| 5,702,432 A | 12/1997 | Chen et al. |
| 5,713,923 A | 2/1998 | Ward et al. |
| 5,724,987 A | 3/1998 | Gevins et al. |
| 5,735,885 A | 4/1998 | Howard, III et al. |
| 5,748,845 A | 5/1998 | Labun et al. |
| 5,758,651 A | 6/1998 | Nygard et al. |
| 5,797,898 A | 8/1998 | Santini, Jr. et al. |
| 5,814,089 A | 9/1998 | Stokes et al. |
| 5,843,093 A | 12/1998 | Howard, III |
| 5,843,142 A | 12/1998 | Sultan |
| 5,855,801 A | 1/1999 | Lin et al. |
| 5,857,978 A | 1/1999 | Hively et al. |
| 5,873,840 A | 2/1999 | Neff |
| 5,928,228 A | 7/1999 | Kordis et al. |
| 5,938,688 A | 8/1999 | Schiff |
| 5,938,689 A | 8/1999 | Fischell et al. |
| 5,938,690 A | 8/1999 | Law et al. |
| 5,995,868 A | 11/1999 | Dorfmeister et al. |
| 6,001,065 A | 12/1999 | DeVito |
| 6,006,124 A | 12/1999 | Fischell et al. |
| 6,016,449 A | 1/2000 | Fischell et al. |
| 6,018,682 A | 1/2000 | Rise et al. |
| 6,024,700 A | 2/2000 | Nemirovski et al. |
| 6,024,702 A | 2/2000 | Iversen |
| 6,027,456 A | 2/2000 | Feler et al. |
| 6,038,477 A | 3/2000 | Kayyali |
| 6,044,292 A | 3/2000 | Heyrend et al. |
| 6,061,593 A | 5/2000 | Fischell et al. |
| 6,086,582 A | 7/2000 | Altman et al. |
| 6,091,015 A | 7/2000 | del Valle et al. |
| 6,092,058 A | 7/2000 | Smyth |
| 6,094,598 A | 7/2000 | Elsberry et al. |
| 6,113,553 A | 9/2000 | Chubbuck |
| 6,125,300 A | 9/2000 | Weijand et al. |
| 6,128,538 A | 10/2000 | Fischell et al. |
| 6,134,474 A | 10/2000 | Fischell et al. |
| 6,154,678 A | 11/2000 | Lauro |
| 6,161,045 A | 12/2000 | Fischell et al. |
| 6,163,725 A | 12/2000 | Peckham et al. |
| 6,164,284 A | 12/2000 | Schulman et al. |
| 6,169,981 B1 | 1/2001 | Werbos |
| 6,171,239 B1 | 1/2001 | Humphrey |
| 6,175,762 B1 | 1/2001 | Kirkup et al. |
| 6,181,965 B1 | 1/2001 | Loeb et al. |
| 6,185,455 B1 | 2/2001 | Loeb et al. |
| 6,216,045 B1 | 4/2001 | Black et al. |
| 6,224,549 B1 | 5/2001 | Drongelen |
| 6,240,315 B1 | 5/2001 | Mo et al. |
| 6,254,536 B1 | 7/2001 | DeVito |
| 6,263,237 B1 | 7/2001 | Rise |
| 6,280,394 B1 | 8/2001 | Maloney et al. |
| 6,304,775 B1 | 10/2001 | Iasemidis et al. |
| 6,309,410 B1 | 10/2001 | Kuzma et al. |
| 6,313,093 B1 | 11/2001 | Frey, II |
| 6,319,241 B1 | 11/2001 | King et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,358,202 B1 | 3/2002 | Arent |
| 6,360,122 B1 | 3/2002 | Fischell et al. |
| 6,366,813 B1 | 4/2002 | DiLorenzo |
| 6,427,086 B1 | 7/2002 | Fischell et al. |
| 6,436,708 B1 | 8/2002 | Leone et al. |
| 6,459,936 B2 | 10/2002 | Fischell et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,510,333 B1 * | 1/2003 | Licata et al. ............ 600/383 |
| 6,549,804 B1 | 4/2003 | Osorio et al. |
| 6,577,893 B1 | 6/2003 | Besson et al. |
| 6,620,415 B2 | 9/2003 | Donovan |
| 6,636,783 B2 | 10/2003 | Yasui et al. |
| 6,658,287 B1 | 12/2003 | Litt et al. |
| 7,010,351 B2 | 3/2006 | Firlik et al. |
| 7,206,632 B2 | 4/2007 | King |
| 7,212,851 B2 | 5/2007 | Donoghue et al. |
| 7,280,870 B2 | 10/2007 | Nurmikko et al. |
| 7,346,396 B2 | 3/2008 | Barriskill et al. |
| 7,392,079 B2 | 6/2008 | Donoghue et al. |
| 7,647,097 B2 | 1/2010 | Flaherty et al. |
| 7,751,877 B2 | 7/2010 | Flaherty et al. |
| 2001/0014818 A1 | 8/2001 | Kennedy |
| 2001/0023368 A1 | 9/2001 | Black et al. |
| 2001/0027336 A1 | 10/2001 | Gielen et al. |
| 2001/0029391 A1 | 10/2001 | Gluckman et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0013612 A1 | 1/2002 | Whitehurst |
| 2002/0016638 A1 | 2/2002 | Mitra et al. |
| 2002/0077534 A1 | 6/2002 | DuRousseau |
| 2002/0077620 A1 | 6/2002 | Sweeney et al. |
| 2002/0082514 A1 | 6/2002 | Williams et al. |
| 2002/0099412 A1 | 7/2002 | Fischell et al. |
| 2002/0169485 A1 | 11/2002 | Pless et al. |
| 2003/0004428 A1 | 1/2003 | Pless et al. |
| 2003/0074032 A1 | 4/2003 | Gliner |
| 2003/0082507 A1 | 5/2003 | Stypulkowski |
| 2003/0083716 A1 | 5/2003 | Nicolelis et al. |
| 2003/0083724 A1 | 5/2003 | Jog et al. |
| 2003/0093129 A1 | 5/2003 | Nicolelis et al. |
| 2003/0139782 A1 | 7/2003 | Duncan et al. |
| 2004/0006264 A1 | 1/2004 | Majarradi et al. |
| 2004/0068204 A1 | 4/2004 | Imran et al. |
| 2004/0073414 A1 | 4/2004 | Bienenstock et al. |
| 2004/0138579 A1 | 7/2004 | Deadwyler et al. |
| 2004/0193068 A1 | 9/2004 | Burton et al. |
| 2004/0267320 A1 | 12/2004 | Taylor et al. |
| 2005/0090756 A1 | 4/2005 | Wolf et al. |
| 2005/0137652 A1 | 6/2005 | Cauller et al. |
| 2005/0273890 A1 | 12/2005 | Flaherty et al. |
| 2006/0029912 A1 | 2/2006 | Kearby et al. |
| 2006/0049957 A1 | 3/2006 | Surgenor et al. |
| 2006/0058627 A1 | 3/2006 | Flaherty et al. |
| 2006/0149338 A1 | 7/2006 | Flaherty et al. |
| 2006/0167371 A1 | 7/2006 | Flaherty et al. |
| 2006/0167530 A1 | 7/2006 | Flaherty et al. |
| 2006/0167564 A1 | 7/2006 | Flaherty et al. |
| 2006/0173259 A1 | 8/2006 | Flaherty et al. |
| 2006/0189900 A1 | 8/2006 | Flaherty |
| 2006/0195042 A1 | 8/2006 | Flaherty |
| 2006/0206167 A1 | 9/2006 | Flaherty et al. |
| 2006/0241356 A1 | 10/2006 | Flaherty |
| 2006/0253166 A1 | 11/2006 | Flaherty et al. |
| 2007/0032738 A1 | 2/2007 | Flaherty et al. |
| 2007/0156126 A1 | 7/2007 | Flaherty |

(56) References Cited

U.S. PATENT DOCUMENTS

| | | |
|---|---|---|
| 2008/0064966 A1 | 3/2008 | Brockway et al. |
| 2010/0023021 A1 | 1/2010 | Flaherty |
| 2010/0063411 A1 | 3/2010 | Donoghue et al. |

FOREIGN PATENT DOCUMENTS

| | | |
|---|---|---|
| WO | WO 01/60445 | 8/2001 |
| WO | WO 01/78833 | 10/2001 |
| WO | WO 01/93756 A2 | 12/2001 |
| WO | WO 02/093312 A2 | 11/2002 |
| WO | WO 02/100267 A1 | 12/2002 |
| WO | WO 03/026739 | 4/2003 |
| WO | WO 03/035165 | 5/2003 |
| WO | WO 03/037231 | 5/2003 |
| WO | WO 03/061465 A2 | 7/2003 |
| WO | WO 20061044793 | 4/2006 |

OTHER PUBLICATIONS

Gernot R. Müller et al., Implementation of a Telemonitoring System for the Control of an EEG-Based Brain Computer Interface, IEEE Transactions on Neural Systems and Rehabilitation Engineering, vol. 11, No. 1, Mar. 2002, (Mar. 2003) pp. 54-59.

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastie et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minessota Epilepsy Group of United and St. Paul Children's Hospital; and Human Motor Control Section, National Institute of Neurological Disorders and Stroke, National Institutes of Health, Electroencephaloraphy and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. ½, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D.M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhom et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2 , Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "intergrating assistive technologies: current practices and future possibilities," Med. Eng. Phys., vol. 18, No. 3, 1996, pp. 193-202.

(56) References Cited

OTHER PUBLICATIONS

Miguel A. L. Nicolelis et al., "Reconstructing the Engram: Simultaneous, Multisite, Many Sinle Neuron Recordings," Nueron, vol. 18, Apr. 1997, pp. 529-537.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Nicolelis, Miguel A.L., "Trigeminal System Plasticity During Facial Anethesia," Department of Health and Human Services, Public Health Service, Grant No. 2 R01 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Wariand et al., "Decoding Visual Information From a Population of Retinal Ganglion Cells," The American Physiological Society, 1997, pp. 2336-2350.

Steven P. Wise et al., "Premotor and Parietal Cortex: Cortiocortical Connectivity and Combinatorial Computations," Annual Review of Neuroscience, vol. 20, 1997, pp. 25-42.

P.R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Nicolelis, Miguel A.L., "Trigeminal System Plasticity During Facial Anethesia," Department of Health and Human Services, Public Health Service, Grant No. 2 R01 DE11451-06, Apr. 1999.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.

M. Maynard et al, "Neuronal Interactions Improve Cortical Population Coding of Movement Direction," The journal of Neuroscience, vol. 19, No. 18, Sep. 15, 1999, pp. 8083-8093.

Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in humans," The Journal of Neuroscience, vol. 20, No. 6, Mar. 15, 2000, pp. 2307-2314.

D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.

Qing Bai et al., "A High-Yield Microassembly Structure for Three-Dimensional Microelectrode Arrays," IEEE Transactions on Biomedical Engineering, vol. 47, No. 3, Mar. 2000, pp. 281-289.

Nicolelis, Miguel A.L., "Trigeminal System Plasticity During Facial Anethesia," Department of Health and Human Services, Public health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related potentials," IEEE Transactions on Rehabilitation Engineering, vol. 8, No. 2, Jun. 2000, pp. 180-185.

Robert E. Isaacs et al., "Work Toward Real-Time Control of a cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University, Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

(56) References Cited

OTHER PUBLICATIONS

John P. Donoghue, "Connecting cortex to machines: recent advances in brain interfaces," Nature Neuroscience Supplement, vol. 5, Nov. 2002, pp. 1085-1088.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter,"Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, Issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

Mohammad Mojarradi, "A Miniaturized Neuroprosthesis Suitable for Implantation Into the Brain," IEEE Transactions on Neural Systems and Rehabilitation Engineering, vol. 11, No. 1, Mar. 2003.

Morten K. Haugland et al., "Cutaneous Whole Nerve Recordings Used for Correction of Footdrop in Hemiplegic Man," IEEE Transactions on Neural Systems and Rehabilitation Engineering, vol. 3, No. 4, Dec. 1995.

Ferdinando Mussa-Ivaldi et al., "Brain-machine interfaces: computational demands and clinical needs meet basic neuroscience,"Trends in Neurosciences, vol. 26, No. 6, Jun. 2003, pp. 329-334.

D.N. Harvey et al., "Multiple-Output Electromyographic Switching System," 1978 ISA, Pittsburgh, PA, 1978, pp. 121-123.

Faisal Karmali et al.," Environmental Control by a Brain-Computer Interface," Proceedings of the $22^{nd}$ Annual EMBS Int'l Conf., Jul. 23-28, 2000, Chicago, IL, pp. 2990-2992.

Alex Mihailidis et al. "Using artificial intelligence to assist people with dementia to be more independent,". Proceedings of the $22^{nd}$ Annual EMBS Int'l Conf., Jul. 23-28, 2000, Chicago, IL, pp. 2993-2996.

Rainer et al., Prospective Coding for Objects in Primate Prefrontal Cortex, The Journal of Neuroscience, The Official Journal of the Society for Neuroscience, vol. 19, No. 13, published Jul. 1, 1999, pp. 5493-5505.

Moxon et al., Neural Prostheses for Restoration of Sensory and Motor Function, Chapter 6 "Designing a Brain Machine Interface for Neuroprosthetic Control", pp. 179-219, Edited by John K. Chapin and Karen A. Moxon of the CRC Press in 2001.

Chapin et al., Neural Prostheses for Restoration of Sensory and Motor Function, Chapter 8 "Brain Control of Sensorimotor Prostheses", pp. 235-260, Edited by John K. Chapin and Karen A. Moxon of the CRC Press in 2001.

Ludvig, Neural Prostheses for Restoration of Sensory and Motor Function, Chapter 9 Drug Deliveries into the Microenvironment of Electrophysiologically Monitored Neurons in the Brain of Behaving Rats and Monkeys, pp. 263-282, Edited by John K. Chapin and Karen A. Moxon of the CRC Press in 2001.

Gao et al., Advances in Neural Information Processing Systems 14: Proceedings, vol. 1, "Probabilistic Inference of Hand Motion from Neural Activity in Motor Cortex", Edited Dietterich et al., total of 8 pages, Accessed May 1, 2013, http://cs.brown.edu/~black/Papers/NIPS14.pdf.

Norretranders, The User Illusion: Cutting Consciousness Down to Size, Chapter 12, "The Origin of Consciousness", pp. 310-328, published Aug. 26, 1999 by the Penguin Group.

* cited by examiner

BIOLOGICAL INTERFACE SYSTEM

This application claims the benefit of priority under 35 U.S.C. §119(e) of U.S. provisional application No. 60/615,629, filed Oct. 4, 2004.

DESCRIPTION OF THE INVENTION

1. Field of the Invention

The present invention relates to biological interface systems that include one or more devices controlled by processed multicellular signals of a patient. A processing unit produces a control signal based on multicellular signals received from a sensor comprising multiple electrodes. More particularly, the system includes numerous components to provide enhanced utility and improved safety.

2. Description of Related Art

Biological interface devices, for example neural interface devices, are currently under development for numerous patient applications including restoration of lost function due to traumatic injury or neurological disease. Sensors, such as electrode arrays, implanted in the higher brain regions that control voluntary movement, can be activated voluntarily to generate electrical signals that can be processed by a biological interface device to create a thought invoked control signal. Such control signals can be used to control numerous devices including computers and communication devices, external prostheses, such as an artificial arm or functional electrical stimulation of paralyzed muscles, as well as robots and other remote control devices. Patient's afflicted with amyotrophic lateral sclerosis (Lou Gehrig's Disease), particularly those in advanced stages of the disease, would also be applicable to receiving a neural interface device, even if just to improve communication to the external world, including Internet access, and thus improve their quality of life.

Early attempts to utilize signals directly from neurons to control an external prosthesis encountered a number of technical difficulties. The ability to identify and obtain stable electrical signals of adequate amplitude was a major issue. Another problem that has been encountered is caused by the changes that occur to the neural signals that occur over time, resulting in a degradation of system performance. Neural interface systems that utilize other neural information, such as electrocorticogram (ECoG) signals, local field potentials (LFPs) and electroencephalogram (EEG) signals have similar issues to those associated with individual neuron signals. Since all of these signals result from the activation of large groups of neurons, the specificity and resolution of the control signal that can be obtained is limited. However, if these lower resolution signals could be properly identified and the system adapt to their changes over time, simple control signals could be generated to control rudimentary devices or work in conjunction with the higher power control signals processed directly from individual neurons.

Commercialization of these neural interfaces has been extremely limited, with the majority of advances made by universities in a preclinical research setting. As the technologies advance and mature, the natural progression may be to more sophisticated human applications, such as those types of devices regulated by various governmental regulatory agencies including the Food and Drug Administration in the United States.

When sophisticated biological interface systems are commercially available it may become important for these systems to include numerous safety features required in the various locations of patient care and other patient settings. Also, systems which allow multiple devices to be controlled in a safe and reliable manner may be mandated. Convenience, flexibility and simplified use for the patient, their caregivers and family members may also be a requirement.

SUMMARY OF THE INVENTION

According to a first aspect of the invention, a biological interface system for collecting multicellular signals emanating from one or more living cells of a patient and for transmitting processed signals to control a device is disclosed. The biological interface system comprises a sensor for detecting the multicellular signals. The sensor comprises a plurality of electrodes that are configured to detect the multicellular signals. The system further comprises a processing unit for receiving the multicellular signals from the sensor, for processing the multicellular signals to produce processed signals, and for transmitting the processed signals to the controlled device. The system further includes the controlled device for receiving the processed signals. The processing unit includes an implanted portion, said implanted portion comprising a first communication transmitter and a second communication transmitter. The first communication transmitter and the second communication transmitter are configured to independently transmit information to one or more devices external to the patient.

According to a second aspect of the invention, a biological interface system for collecting multicellular signals emanating from one or more living cells of a patient and for transmitting processed signals to control a device is disclosed. The system comprises a first sensor for detecting the multicellular signals, the sensor comprising a plurality of electrodes to allow for detection of the multicellular signals and a second sensor for detecting an additional parameter. The system also includes a processing unit for receiving the multicellular signals from the first sensor and for processing the multicellular signals to produce processed signals. The processing unit includes an implanted portion. The system further includes the controlled device for receiving the processed signals. The implanted portion of the processing unit also receives signals from said second sensor.

According to another aspect of the invention, a biological interface system for collecting multicellular signals emanating from one or more living cells of a patient and for transmitting processed signals to control a device is disclosed. The system comprises a sensor for detecting the multicellular signals. The sensor comprises a plurality of electrodes that detect the multicellular signals. The system further comprises a processing unit for receiving the multicellular signals from the sensor and for processing the multicellular signals to produce processed signals. The processing unit comprises an impedance analysis device for measuring the impedance of an electrical path between one or more of the sensor electrodes and a separate location. The system further includes the controlled device for receiving the processed signals.

According to another aspect of the invention, a biological interface system for collecting multicellular signals emanating from one or more living cells of a patient and for transmitting processed signals to control a device is disclosed. The system comprises a sensor for detecting the multicellular signals. The sensor comprises a plurality of electrodes that detect the multicellular signals. The system further includes a processing unit for receiving the multicellular signals from the sensor and for processing the multicellular signals to produce processed signals. The processing unit comprises an electronic module for processing signals. The system further includes a controlled device for receiving the processed signals. The electronic module includes first electrostatic discharge protection circuitry which prevents electrostatic discharge energy from damaging one or more components of the electronic module. The electronic module further includes second electrostatic discharge protection circuitry which prevents electrostatic discharge energy from damaging tissue of the patient.

According to yet another aspect of the invention, a cellular access system comprising a sensor for placing multiple electrodes in close proximity to living cells below a tissue surface of a patient is disclosed. The sensor comprises a base of material having a top surface and a bottom surface. A plurality of elongate projections are mounted to the base and extend from the bottom surface of the base. One or more of said projections include at least one electrode along its length. The system further includes connection member linked with the electrodes for providing electrical connection to each of the electrodes. The system further includes a protective cap which is configured to protect one or more of the projections from damage. The mounting pattern of the projections defines a periphery, and the base further includes a flange portion extending radially outward from at least a portion of the mounting pattern periphery. The protective cap engages with the flange portion of the base of the sensor.

According to yet another aspect of the invention, a cellular access system for implanting in a patient is disclosed. The system comprises a sensor comprising a plurality of electrodes that allow chronic access of cells. The sensor comprises a base of material having a top surface and a bottom surface. A plurality of elongate projections are mounted to the base and extend from the bottom surface of the base. One or more of the projections include at least one electrode along its length. The system further includes signal connection member linked with the electrodes for providing electrical connection to each of the electrodes. An elongate electrical conduit comprising a bundle of filamentous conductors, one end of each of the filamentous conductors are electrically connected to the signal connection member of the sensor. The electrical conduit includes at least one fixation point along its length.

According to yet another aspect of the invention, a cellular access system for implanting in a patient is disclosed. The system comprises a sensor for placing multiple electrodes in close proximity to living cells below a tissue surface. The sensor comprises a base of material having a top surface and a bottom surface. A plurality of elongate projections are mounted to the base and extend from the bottom surface of the base. One or more of the projections include at least one electrode along its length. The system further includes signal connection member linked with the electrodes for providing electrical connection to each of the electrodes. The system further includes a planar electrical conduit comprising a plurality of conductors. Each conductor is electrically connected to the one or more conductive pads of the sensor. The planar electrical conduit includes an expandable portion along its length.

According to yet another aspect of the invention, a cellular access system for implanting in a patient is disclosed. The system comprises a sensor for placing multiple electrodes in close proximity to living cells below a tissue surface. The sensor comprises a base of material having a top surface and a bottom surface, the top surface including a pattern of electrical conductors. A plurality of elongate projections are mounted to the base and extend from the bottom surface of the base. One or more of the projections include at least one electrode along its length. The system further comprises signal connection member linked with the electrodes for providing electrical connection from each of said electrodes to said pattern of electrical conductors on the top surface of the base. The system further includes a planar electrical conduit including a proximal end and a distal end. The planar electrical conduit comprises a plurality of conductors. The planar electrical conduit includes on its proximal end a pattern of conductors, said pattern matching and being electrically connected to the pattern of conductors on the top surface of the base of the sensor.

According to yet another aspect of the invention, an inserter for implanting an electrode array in a biological tissue is disclosed. The inserter comprises a casing having first and second ends and enclosing a chamber. A piston is disposed within the casing and is slidable between a first and a second position. The inserter further includes piston actuator operably associated with the piston for urging the piston to the second position. The inserter further includes a piston attachment member for attaching the piston to the electrode array to be implanted.

Both the foregoing general description and the following detailed description are exemplary and are intended to provide further explanation of the embodiments of the invention as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings.

DESCRIPTION OF THE EMBODIMENTS

Figure 1:
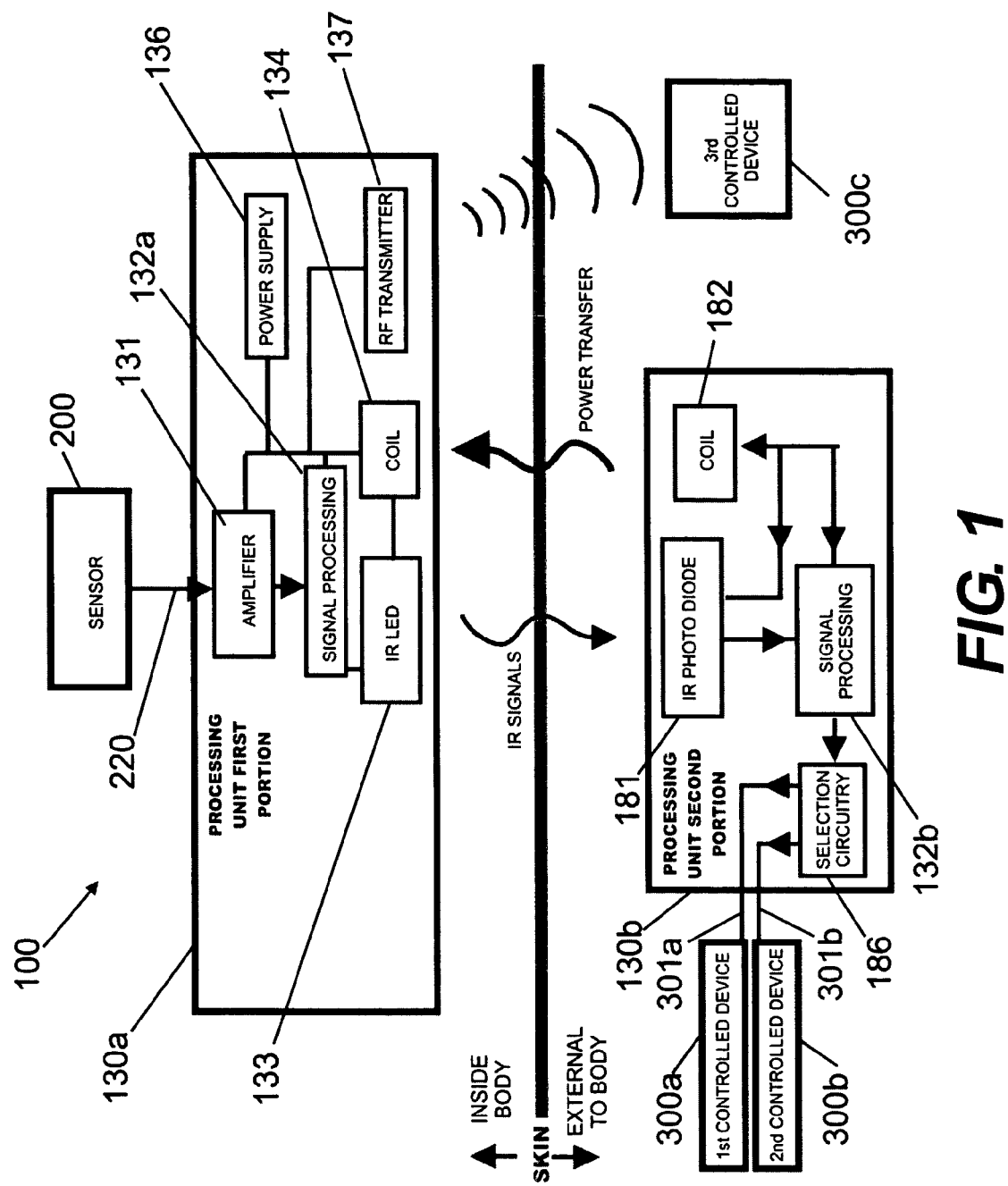
FIG. 1 illustrates a schematic representation of the biological interface system consistent with the present invention.

To facilitate an understanding of the invention, a number of terms are defined immediately herebelow.

Definitions

As used herein, the term "biological interface system" refers to a neural interface system, brain machine interface, or any other system that interfaces with living cells that produce electrical activity or cells that produce other types of detectable signals.

As used herein, the term "cellular signals" refers to subcellular signals, intracellular signals, extracellular signals, single cell signals and signals emanating from one or more cells. The term "subcellular signals," as used herein, refers to: a signal derived from a part of a cell; a signal derived from one particular physical location along or within a cell; a signal from a cell extension, such as a dendrite, dendrite branch, dendrite tree, axon, axon tree, axon branch, pseudopod or growth cone; or signals from organelles, such as golgi apparatus or endoplasmic reticulum. The term "intracellular signals," as used herein, refers to a signal that is generated within a cell or by the entire cell that is confined to the inside of the cell up to and including the membrane. The term "extracellular signals," as used herein, refers to signals generated by one or more cells that occur outside of the cell(s). "Cellular signals" generally include, but are not limited to, signals or combinations of signals that emanate from any living cell. Specific examples of "cellular signals" include but are not limited to: neural signals; cardiac signals including cardiac action potentials; electromyogram (EMG) signals; glial cell signals; stomach cell signals; kidney cell signals; liver cell signals; pancreas cell signals; osteocyte cell signals; sensory organ cell signals such as signals emanating from the eye or inner ear; and tooth cell signals. The term "neural signals," as used herein, refers to: neuron action potentials or spikes; local field potential (LFP) signals; electroencephalogram (EEG) signals; electrocorticogram signals (ECoG); and signals that are between single neuron spikes and EEG signals.

As used herein, the term "multicellular signals" refers to signals emanating from two or more cells, or multiple signals emanating from a single cell.

As used herein, the term "patient" refers to any animal, such as a mammal and preferably a human. Specific examples of "patients" include but are not limited to: individuals requiring medical assistance; healthy individuals; individuals with limited function; and in particular, individuals with lost function due to traumatic injury or neurological disease.

As used herein, the term "configuration" refers to any alteration, improvement, repair, calibration or other system modifying event whether manual in nature or partially or fully automated.

As used herein, the term "discrete component" refers to a component of a system such as those defined by a housing or other enclosed or partially enclosed structure, or those defined as being detached or detachable from another discrete component. Each discrete component can transmit information to a separate component through the use of a physical cable, including one or more of electrically conductive wires or optical fibers, or transmission of information can be accomplished wirelessly. Wireless communication can be accomplished with a transceiver that may transmit and receive data such as through the use of "Bluetooth" technology or according to any other type of wireless communication means, method, protocol, or standard, including, for example, code division multiple access (CDMA), wireless application protocol (WAP), Infrared or other optical telemetry, radio frequency or other electromagnetic telemetry, ultrasonic telemetry, or other telemetric technologies.

General Description of the Embodiments

Systems, system components and methods consistent with the invention detect cellular signals generated within a patient's body and implement various signal processing techniques to generate processed signals for transmission to one or more devices to be controlled. The system includes a sensor comprising a plurality of electrodes that detect multicellular signals from one or more living cells, such as from the central or peripheral nervous system of a patient. The system further includes a processing unit that receives and processes the multicellular signals and transmits a processed signal to a controlled device. The processing unit utilizes various electronic, mathematic, neural net, and/or other signal processing techniques in producing the processed signal. Examples of controlled devices include but are not limited to prosthetic limbs, ambulation vehicles, communication devices, robots, computers, or other controllable devices.

Detailed Description of the Embodiments

Reference may now be made in detail to the exemplary embodiments consistent with the present invention, examples of which are illustrated in the accompanying drawings. Wherever possible, the same reference numbers may be used throughout the drawings to refer to the same or like parts.

Referring now to FIG. 1, a schematic representation of a biological interface system 100 may comprise implanted components and components external to the body of patient, the boundary defined schematically by a horizontal line labeled "SKIN". The system 100 comprises sensor 200 that includes a plurality of electrodes, not shown, for detecting multicellular signals. Sensor 200 may take various geometric forms and include numerous materials of construction, described in detail in reference to subsequent figures of this application. All exposed surfaces, such as surfaces that come in contact with tissue or bodily fluids, comprise a biocompatible material. In an exemplary embodiment, sensor 200 includes a ten by ten (10×10) matrix of electrodes. The electrodes are positioned at the tip of individual projections. By way of example only, these projections are spaced at approximately 400 µm with a height of 1.0 to 1.5 mm, and the electrodes have an impedance between 100 kOhm and 1 MOhm. In an exemplary embodiment, one or more projections is tapered along its length. Sensor 200 may be placed at various locations internal and/or external to a patient, and may comprise multiple discrete components.

The system 100 also comprises a processing unit that receives the multicellular signals from sensor 200, which utilizes one or more signal processing techniques to produce processed signals. Depicted in FIG. 1 is processing unit first portion 130*a* and processing unit second portion 130*b* that are each a component of the processing unit. Additional components may also be part of the processing unit. All of the components collectively perform the receiving of the multicellular signals and the production of the processed signals. Discrete components of the processing unit can be implanted within the patient, be external to the patient, or protrude through the skin of the patient.

As depicted in FIG. 1, processing unit first portion 130*a* is implanted under the skin of the patient, such as on top of the skull of the patient under the scalp. In an exemplary embodiment, sensor 200, also implanted, is placed within the skull such that one or more electrodes are placed within a cortical layer of the brain. Wire bundle 220, a single or multi-conductor cable, is attached to sensor 200 and processing unit first portion 130*a*. In an exemplary embodiment, wire bundle 220 is resiliently flexible, along at least a portion of its length. In an alternative embodiment, wire bundle 220 is plastically deformable along at least a portion of its length. In another exemplary embodiment, wire bundle 220 includes resiliently flexible portions and plastically deformable portions along its length. Wire bundle 220 attaches to one or more electrodes of sensor 200 and may include other filamentous conductors or filamentous conduits such as a conductor that provides a reference signal at a location in proximity to the electrodes of sensor 200. In an exemplary embodiment, multiple individual electrodes of sensor 200 are attached each to individual conductors of wire bundle 220, and wire bundle 220 includes at least two conductors that do not attach to electrodes that are placed to provide relevant reference signals for one or more signal processing functions. In an exemplary embodiment, the conductive wires of wire bundle 220 have a diameter of approximately 25 µm and comprise a blend of gold and palladium. Wire bundle 220 conductors are attached at their other ends to processing unit fist portion 130*a*, and the conductors and housing of processing unit first portion 130*a* are sealed such that the signals, conductive surfaces, and other internal components of wire bundle 220 and processing unit first portion 130*a* are appropriately protected from contamination by body fluids and other contaminants.

Processing unit first portion 130*a* includes amplifier 131 for amplifying the cellular signals, which is preferably an amplifier with a gain of at least eighty and preferably one hundred, a working frequency range of 0.001 Hz to 7.2 kHz, a power requirement of approximately 1.6V and a power dissipation of approximately 30 mW. Processing unit first portion 130*a* further includes additional signal processing element 132*a*. Various signal processing techniques can be utilized including but not limited to: filtering, sorting, conditioning, translating, interpreting, encoding, decoding, combining, extracting, sampling, multiplexing, analog-to-digital converting, digital to analog converting, mathematically transforming and/or otherwise processing multicellular signals to generate a control signal for transmission to a controlled device. In an exemplary embodiment, signal processing element 132*a* includes a multiplexor function, such as a thirty-two to one multiplexor with a 1 MHz switching frequency. In another exemplary embodiment, signal processing element 132*a* includes an analog-to-digital converter with twelve-bit resolution that can process 1 megasample per second for thirty-two channels.

It is desirable that all implanted components avoid the need to protrude through the skin of the patient, such as for cosmetics and reduced infection risk. In order for processing unit first portion 130*a* to transmit one or more signals to an external component, processing unit first portion 130*a* may provide two means of wireless information transfer. RF Transmitter 137 provides long range communication for transmission of processed signals and other signals to an external device such as a controlled device. In addition, IR transmitter 133 is incorporated into the implant. IR transmitter 133 includes preferably one or more infrared (IR) light emitting diodes (LEDs). Such IR transmissions may penetrate through a finite amount of tissue, such as the scalp, at high data rates up to 50 megabits per second and above. In an exemplary embodiment, IR transmitter 133 transmits data at 40 megabit per second utilizing direct modulation. IR transmitter 133 receives information from signal processing element 132*a*, and transmits the information to processing unit second portion 130*b* by way of its integrated receiver, such as, for example, IR receiver 181. Both IR transmitter 133 and IR receiver 181 can include lenses, filters, and other optical components to focus, collect, capture or otherwise improve the IR transmission and receiving performance. In an exemplary embodiment, RF transmitter 137 is used to send time-coded cellular or multicellular activity, such as time-coded neural firing from multiple neurons such as thirty to one hundred neurons. RF transmitter 137 can also be used to send processed signals directly to the controlled device. In another exemplary embodiment, IR transmitter 133 is used to send analog cellular information, such as analog information from thirty to one hundred neurons. Large data rate communications using IR transmitter 133 are appropriate for calibration and other system configuration procedures, system diagnostic procedures, and for transmission of processed signals of the present invention requiring a high data rate. In another exemplary embodiment, IR transmitter 133 is used to control one type of controlled device, such as a controlled device requiring high baud rate transmission through the skin, and RF transmitter 137 is used to control another type of controlled device, such as a controlled device requiring a lower baud rate transmission through the skin, or to communicate via a cellular telephone network. Wireless control of controlled devices at a distance of ten to twenty feet or more from the patient can be accomplished with RF transmitter 137. In another exemplary embodiment, processing unit first portion 130*a* further includes an integral battery, power supply 136, such as a rechargeable battery, that can be used to supply power to RF transmitter 137 and signal processing circuitry 132*a*. In another exemplary embodiment, RF transmitter 137 is a transceiver. In another exemplary embodiment, IR transmitter 133 is a transceiver.

Processing unit second portion 130*b*, a component external to the body of the patient, is affixed or otherwise placed at a location in close proximity to the location of processing unit first portion 130*a*'s transmitter, IR transmitter 133. In an exemplary embodiment, processing unit first portion 130a is placed in a recess made in the skull, during a surgical procedure, at a location near to and above the ear of the patient. Processing unit second portion 130b is placed on the head just above the ear such that IR receiver 181 is at a location near aligned with IR transmitter 133, such as a line of site distance of approximately 4 mm. Information transfer takes place such as that using various error detection schemes, handshaking functions and other communication and error checking protocols such as ANSI X3.230 protocol and other protocols well known to those of skill of the art and applicable to digital, analog and combined digital/analog critical use communications.

Processing unit first portion 130a may include one or more additional elements, not shown, but included within, on the surface of, or attached to processing unit first portion 130a. Such elements may include but are not limited to: a temperature sensor, a pressure sensor, a strain gauge, an accelerometer, a volume sensor, an electrode, an array of electrodes, an audio transducer, a mechanical vibrator, a drug delivery device, a magnetic field generator, a photo detector element, a camera or other visualization apparatus, a wireless communication element, a light producing element, an electrical stimulator, a physiologic sensor, a heating element and a cooling element. Depicted in FIG. 1, processing unit first portion 130a includes a coil, implanted coil assembly 134, the assembly being configured to receive and convert electromagnetic signals from a device external to the body of the patient, preferably processing unit second portion 130b. Processing unit second portion 130b, also includes a coil assembly 182, which is oriented within a housing of processing unit second portion 130b such that when IR Receiver 181 is near aligned with IR Transmitter 133, coil assembly 182 can be near aligned with implanted coil assembly 134. The coil in implanted coil assembly 134 is preferably approximately 1 inch in diameter.

Through inductive coupling, power can be transferred from processing unit second portion 130b to processing unit first portion 130a by supplying a driving signal to coil assembly 182, a wireless power receiving element, that generates an electromagnetic field that, through inductive coupling, generates power in implanted coil assembly 134. This captured energy is converted to usable power by circuitry incorporated into implanted coil assembly 134 and can be used to power one or more elements of processing unit first portion 130a and/or recharge an integrated power supply, not shown. In the preferred embodiment shown in FIG. 1, if power supply 136 is depleted or otherwise cannot supply power, power can be supplied to processing unit first portion 130a via coil assembly 182 to allow full function of the system. In another exemplary embodiment, information can be transferred from processing unit second portion 130b to processing unit first portion 130a by modulating the waveform with circuitry included in coil assembly 182 or another component of processing unit second portion 130b. The transmission is received and decoded by the coil and circuitry of implanted coil assembly 134. This modulation pattern can easily be encoded and decoded to provide means of sending information to the implant, such as in a configuration procedure, embedding of a unique identifier, or other procedure.

Processing unit second portion 130b also includes signal processing element 132b. Signal processing can include one or more of the processes listed above in reference to signal processing element 132a and preferable includes at least a decoding function or a multiplexing function. The signal processing element 132b, in combination with signal processing element 132a of processing unit first portion 130a, may complete the processing unit function of the system of the present invention such that the two signal processing elements 132a, 132b in combination produce the processed signals that may be used to control a first controlled device 300a and a second controlled device 300b. Processing unit second portion 130b may include wireless communication means, not shown, or wired communication means to transmit the processed signals to the controlled devices of the system. The various embodiments and elements utilizing wireless communication means can utilize radiofrequency (RF), infrared, ultrasound, microwave, magnetic, electromagnetic, other data transmission technologies that do not require a physical conductor or combinations thereof. The various embodiments and elements utilizing wired communication means can comprise electrical conductors, optical fibers, sound wave guiding conduits, other physical cables and conductors or combinations of the preceding. Alternatively or additionally, RF transmitter 137 of processing unit first portion 130a may send processed signals via RF communications to a third controlled device 300c. Alternatively or additionally, IR transmitter 133 of processing unit first portion 130a may send processed signals via infrared communications to a controlled device, not shown.

System 100 can have one or more operators including but not limited to: the patient; a technician; a clinician; a caregiver and a family member of the patient. In an exemplary embodiment, processed signals can be sent to multiple controlled devices, such as multiple external devices with wireless transceivers, such that processed signals control multiple controlled devices simultaneously. When multiple controlled devices are controlled simultaneously, the processed signals sent to each controlled device may be identical or different.

Referring again to FIG. 1, processing unit second portion 130b connects to first controlled device 300a with cable 301a, and processing unit second portion 130b connects to second controlled device 300b with cable 301b. Both cable 301a and cable 301b receive processed signals as determined by conductor selection circuitry 186. Conductor selection circuitry 186 may include solid state relays, transistor switches, or other signal switching or controlling circuitry well known to those of skill in the art. Based on the information received from selector module 400, processed signals are sent to first controlled device 300a and/or second controlled device 300b as the appropriate connections are made in conductor selection circuitry 186.

A method of controlling one or more specific controlled devices can be accomplished by a unique identifier contained in the processed signals transmitted to the controlled devices wherein the controlled devices includes means of identifying and/or differentiating the appropriate identifier. This identification confirming means may be a part of each controlled device, or a separate discrete component in communication with one or more controlled devices. When a controlled device receives the proper unique identifier, control may commence. The transmission of the identifier can be at the outset of control, or may be required on a continuous basis, such as by being included with individual packets of transmitted information. A limited transmission or one-time sending of the identifier can be accompanied by an initiation command to start control. Similar approaches can be performed to cease control of one or more controlled devices. In continuous identifier transmission, cessation of control is accomplished by discontinuation of transmission of the identifier with the individual packets. In limited or one-time transmission of the identifier, the identifier can be resent and accompanied by a cessation command.

The unique controlled device identifier approach is a preferred method when processed signals are transmitted to controlled devices with wireless communication means, such that when two or more controlled devices may both be in proximity to receive the processed signals but only the appropriate one or more controlled devices may be controlled by the processed signals. An alternative method of controlling one or more specific controlled devices involves directing the processed signals to one or more specific conductors connected to one or more specific controlled devices.

Figure 2:
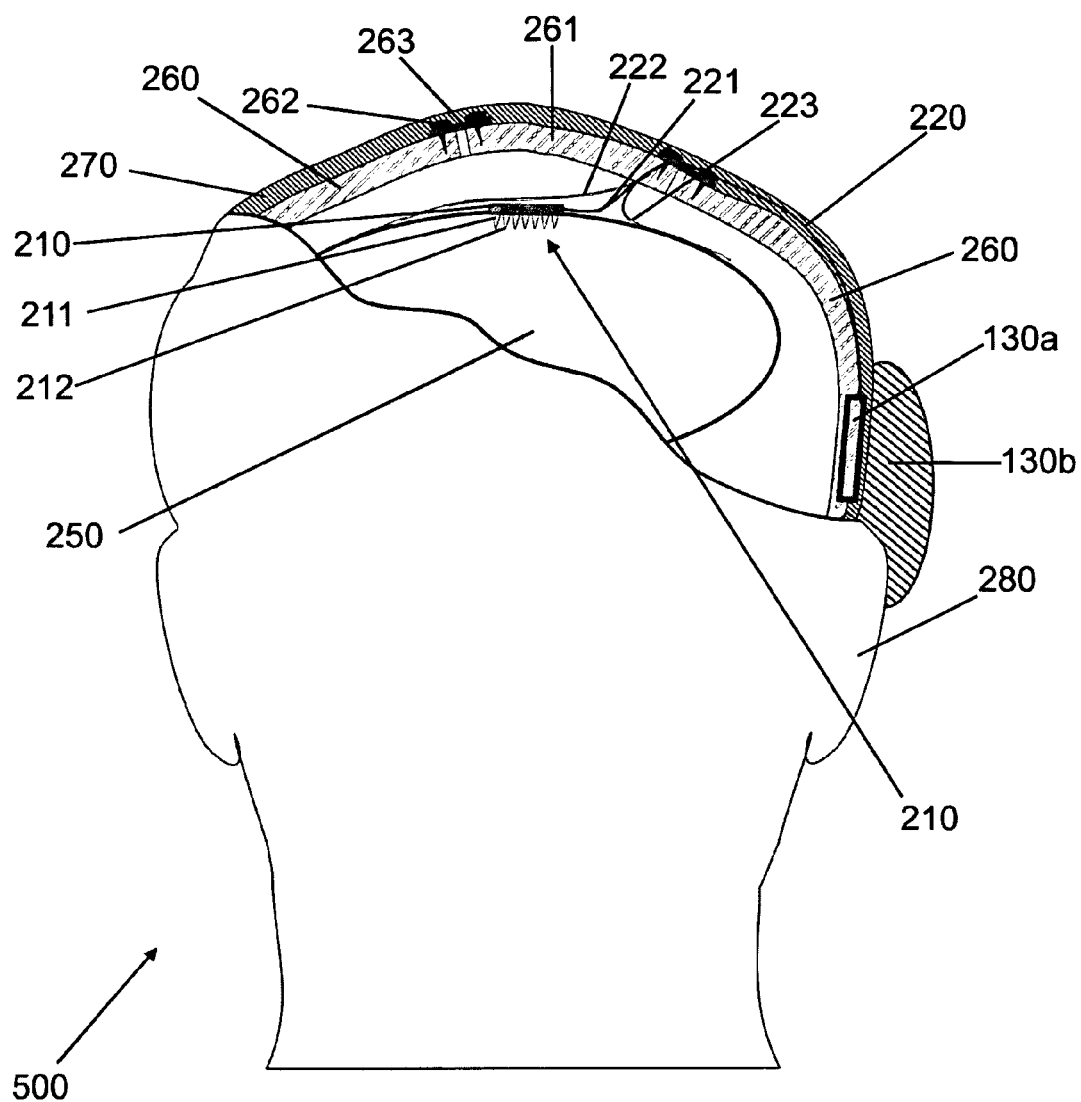
FIG. 2 illustrates an exemplary embodiment of a portion of the biological system, including sensor electrodes implanted in the brain of a patient and a first portion of a processing unit implanted on the skull of the patient, and a second portion of the processing unit placed near the ear of the patient, consistent with the present invention.

Referring now to FIG. 2, a brain implant apparatus consistent with an embodiment of the present invention is illustrated. As shown in FIG. 2, the system includes a sensor, electrode array 210 that has been inserted into a brain 250 of patient 500, through an opening surgically created in skull 260. Array 210 includes a plurality of electrodes 212 for detecting electrical brain signals or impulses. Array 210 may be placed in any location of a patient's brain allowing for electrodes 212 to detect these brain signals or impulses. In an exemplary embodiment, electrodes 212 can be inserted into a part of brain 250 such as the cerebral cortex. Other locations for array 210, such as those outside of the cranium, can record cellular signals as well. Non-penetrating electrode configurations, such as subdural grids, cuff electrodes, and scalp electrodes are applicable both inside the cranium such as to record local field potentials (LFPs), in, on, or near peripheral nerves, and on the surface of the scalp such as to record electroencephalogram signals (EEGs). Though FIG. 2 depicts the sensor as a single discrete component, in alternative embodiments the sensor may comprise multiple discrete components. Multiple sensor components can be implanted entirely in the brain or at an extracranial location, or the multiple discrete sensor components can be placed in any combination of locations.

Electrode array 210 serves as the sensor for the biological interface system of the present invention. While FIG. 2 shows electrode array 210 as eight electrodes 212, array 210 may include one or more electrodes having a variety of sizes, lengths, shapes, forms, and arrangements. For example, the electrode array 210 may be a ten by ten array of electrodes. Moreover, array 210 may be a linear array (e.g., a row of electrodes) or a two-dimensional array (e.g., a matrix of rows and columns of electrodes), or wire or wire bundle electrodes. An individual wire lead may include a plurality of electrodes. Electrodes may have the same materials of construction and geometry, or there may be varied materials and/or geometries used in one or more electrodes. Each electrode 212 of FIG. 2 extends into brain 250 to detect one or more cellular signals such as those generated from the neurons located in proximity to the each electrode 212's placement within the brain. Neurons may generate such signals when, for example, the brain instructs a particular limb to move in a particular way. In an exemplary embodiment, the electrodes reside within the arm or leg portion of the motor cortex of the brain.

In the embodiment shown in FIG. 2, array 210 includes sensor substrate 210 that includes multiple projections 211 emanating from a base. The base can have a rigid construction, a flexible construction, or have combinations of rigid and flexible portions. At the end of each projection 211 is an electrode, electrode 212. Multiple electrodes, not shown, may be included along the length of one or more of the projections 211. Projections 211 may be rigid, semi-flexible or flexible, the flexibility such that each projection 211 can still penetrate into neural tissue, potentially with an assisting device or with projections that temporarily exist in a rigid condition. One or more projections 211 may be void of any electrode, such projections potential including anchoring device such as bulbous tips or barbs, not shown. Array 210 may be passed through a hole cut into skull 260, during a procedure known as a craniotomy, and inserted into brain 250, such that the projections pierce into brain 250 and sensor substrate 210 remains in close proximity to or in light contact with the surface of brain 250. The processing unit of the present invention includes processing unit first portion 130a, placed in a surgically created recess in skull 260 at a location near patient 500's ear 280. Processing unit first portion 130a receives cellular signals from array 210 via wire bundle 220 (e.g., a multi-conductor cable). Processed signals are produced by processing unit first portion 130a and other processing unit components, such as processing unit second portion 130b located on the external skin surface of patient 500 near ear 280. The multicellular signals received from array 210 include a time code of brain activity. Processing unit first portion 130a and processing unit second portion 130b have similar elements and functionality to the identically referenced items of FIG. 1.

In the preferred embodiment depicted in FIG. 2, bone flap 261, the original bone portion removed in the craniotomy, may be used to close the hole made in the skull 260 during the craniotomy, obviating the need for a prosthetic closure implant. Bone flap 261 is attached to skull 260 with one or more straps, bands 263, that are preferably titanium or stainless steel. Band 263 is secured to bone flap 261 and skull 260 with screw 262 (e.g., bone screws). Wire bundle 220 passes between bone flap 260 and the hole cut into skull 260. During the surgical procedure, a recess may be made in skull 260 such that processing unit first portion 130a could be placed in the recess, allowing scalp 270 to be relatively flat in the area proximal to processing unit first portion 130a. A long incision in the scalp between the craniotomy site and the recess can be made to place processing unit first portion 130a in the recess. Alternatively, an incision can be made to perform the craniotomy, and a separate incision can be made to form the recess. The processing unit first portion 130a and wire bundle 220 can be tunneled under the scalp to the desired location. Processing unit first portion 130a is attached to skull 260 with one or more bone screws or a biocompatible adhesive, not shown.

In an alternative embodiment, processing unit first portion 130a may be placed entirely within skull 260 or be shaped and placed to fill the craniotomy hole instead of bone flap 261. Processing unit first portion 130a can be placed in close proximity to array 210, or a distance of 5-20 cm can separate the two components. Processing unit second portion 130b, placed at a location proximate to implanted processing unit first portion 130a but external to patient 500, receives information from processing unit first portion 130a via wireless communication through the skin. Processing unit second portion 130b can include means of securing to patient 500 including but not limited to: an ear attachment mechanism; a holding strap; adhesives; magnets, or other suitable means. Processing unit second portion 130b, includes, in addition to wireless information receiving means, power transfer means, signal processing circuitry, an embedded power supply such as a battery, and information transfer means. The information transfer means of processing unit second portion 130b may include means to transfer information to one or more of: implanted processing unit first portion 130a; a different implanted device; and an external device such as an additional component of the processing unit, a controlled device, or a computer device such as a computer with Internet access.

Referring back to FIG. 2, electrodes 212 transfer the detected cellular signals to processing unit first portion 130a via array wires 221 and wire bundle 220. Wire bundle 220 includes multiple conductive elements (e.g., array wires 221) that may include a conductor for each electrode of array 210. Also included in wire bundle 220 are two conductors, first reference wire 222 and second reference wire 223 each of which is placed in an area in relative proximity to array 210. First reference wire 222 and second reference wire 223, may be redundant, and provide reference signals used by one or more signal processing elements of the processing unit to process the cellular information detected by one or more electrodes.

Each projection 211 of electrode array 210 may include a single electrode, such as an electrode at the tip of the projection 211, or multiple electrodes along the length of each projection. Each electrode 212 may be used to detect the firing of one or more neurons, as well as other cellular signals such as those from clusters of neurons. Additional electrodes, not shown, such as those integrated into subdural grids, scalp electrodes, cuff electrodes, scalp electrodes, and other electrodes, can also detect cellular signals emanating from the central or peripheral nervous system, or other part of the body generating cellular signals, such that the processing unit uses these signals to produce the processed signals to send to the controlled device, not shown. Examples of detected signals include but are not limited to: neuron spikes, electrocorticogram signals, local field potential signals, electroencephalogram signals, and other signals between single neuron spikes and electroencephalogram signals. The processing unit may assign one or more specific cellular signals to a specific use, such as a specific use correlated to a patient imagined event. In an exemplary embodiment, the one or more cellular signals assigned to a specific use are under voluntary control of the patient. In an alternative embodiment, cellular signals are transmitted to processing unit 130 via wireless technologies, such as infrared communication, such transmissions penetrating the skull of the patient, and obviating the need for wire bundle 220, array wires 221, and any physical conduit passing through skull 260 after the surgical implantation procedure is completed.

Referring back to FIG. 2, processing unit first portion 130*a* and processing unit second portion 130*b* may independently or in combination preprocess the received cellular signals (e.g., impedance matching, noise filtering, or amplifying), digitize them, and further process the cellular signals to extract neural information that processing unit second portion 130*b* may then transmit to an external device (not shown), such as a further processing device and/or any device to be controlled by the processed multicellular signals. For example, the external device may decode the received neural information into control signals for controlling a prosthetic limb or limb assist device, for controlling a computer cursor, or the external device may analyze the neural information for a variety of other purposes.

Processing unit first portion 130*a* and processing unit second portion 130*b* may independently or in combination also conduct adaptive processing of the received cellular signals by changing one or more parameters of the system to achieve acceptable or improved performance. Examples of adaptive processing include, but are not limited to, changing a parameter during a system configuration, changing a method of encoding neural information, changing the type, subset, or amount of neural information that is processed, or changing a method of decoding neural information. Changing an encoding method may include changing neuron spike sorting methodology, calculations, thresholds, or pattern recognition. Changing a decoding methodology may include changing variables, coefficients, algorithms, and/or filter selections. Other examples of adaptive processing may include changing over time the type or combination of types of signals processed, such as EEG, LFP, neural spikes, or other signal types.

Processing unit first portion 130*a* and processing unit second portion 130*b* may independently or in combination also transmit signals to one or more electrodes 212 such as to stimulate the neighboring nerves or other cells. Stimulating electrodes in various locations can be used by processing unit 130 to transmit signals to the central nervous system, peripheral nervous system, other body systems, body organs, muscles, and other tissue or cells. The transmission of these signals is used to perform one or more functions including but not limited to: pain therapy, muscle stimulation, seizure disruption, and patient feedback.

Processing unit first portion 130*a* and processing unit second portion 130*b* independently or in combination include signal processing circuitry to perform one or more functions including but not limited to: amplification, filtering, sorting, conditioning, translating, interpreting, encoding, decoding, combining, extracting, sampling, multiplexing, analog-to-digital converting, digital to analog converting, mathematically transforming, and/or otherwise processing cellular signals to generate a control signal for transmission to a controlled device. Processing unit first portion 130*a* transmits raw or processed cellular information to processing unit second portion 130*b* through integrated wireless communication means, such as radiofrequency communications, infrared communications, inductive communications, ultrasound communications, and microwave communications. This wireless transfer allows the array 210 and processing unit first portion 130*a* to be completely implanted under the skin of the patient, avoiding the need for implanted devices that require protrusion of a portion of the device through the skin surface. Processing unit first portion 130*a* may further include a coil, not shown, which can receive power, such as through inductive coupling, on a continual or intermittent basis from an external power transmitting device as has been described in detail in reference to FIG. 1. In addition to or in place of power transmission, this integrated coil and its associated circuitry may receive information from an external coil whose signal is modulated in correlation to a specific information signal. The power and information can be delivered to processing unit first portion 130*a* simultaneously such as through simple modulation schemes in the power transfer that are decoded into information for processing unit first portion 130 to use, store, or facilitate another function. A second information transfer means, in addition to a wireless means such as an infrared led, can be accomplished by modulating a signal in the coil of processing unit first portion 130*a* such that information is transmitted from the implant to an external device including a coil and decoding elements.

In an alternative embodiment, not shown, processing unit first portion 130*a*, and potentially additional signal processing functions, are integrated into array 210, such as through the use of a bonded electronic microchip. In another alternative embodiment, processing unit first portion 130*a* may also receive non-neural cellular signals and/or other biologic signals, such as from an implanted sensor. These signals may be in addition to received neural multicellular signals, and they may include but are not limited to: EKG signals, respiration signals, blood pressure signals, electromyographic activity signals, and glucose level signals. Such biological signals may be used to turn the biological interface system, or one of its discrete components, on or off, to begin a configuration routine, or to start or stop another system function. In another alternative embodiment, processing unit first portion 130*a* and processing unit second portion 130*b* independently or in combination produce one or more additional processed signals, to additionally control the controlled device of the present invention or to control one or more additional controlled devices.

In an alternative embodiment, a discrete component is implanted within the cranium of the patient. For example, array 210 of FIG. 2, a processing unit, or a portion of a processing unit may be implanted in the torso of the patient, and one or more discrete components are external to the body of the patient. The processing unit may receive multicellular signals from the sensor via wired, including conductive wires and optic fibers, or wireless communication.

Each sensor discrete component of the present invention can have as few as a single electrode, with the sensor including multiple sensor discrete components that collectively contain a plurality of electrodes. Each electrode is capable of recording a plurality of neurons, or other electrical activity. In an alternative embodiment, one or more electrodes are included in the sensor to deliver electrical signals or other energy to the tissue neighboring the electrode, such as to stimulate, polarize, hyperpolarize, or otherwise cause an effect on one or more cells of neighboring tissue. Specific electrodes may record cellular signals only, or deliver energy only, and specific electrodes may provide both functions.

Figure 3:
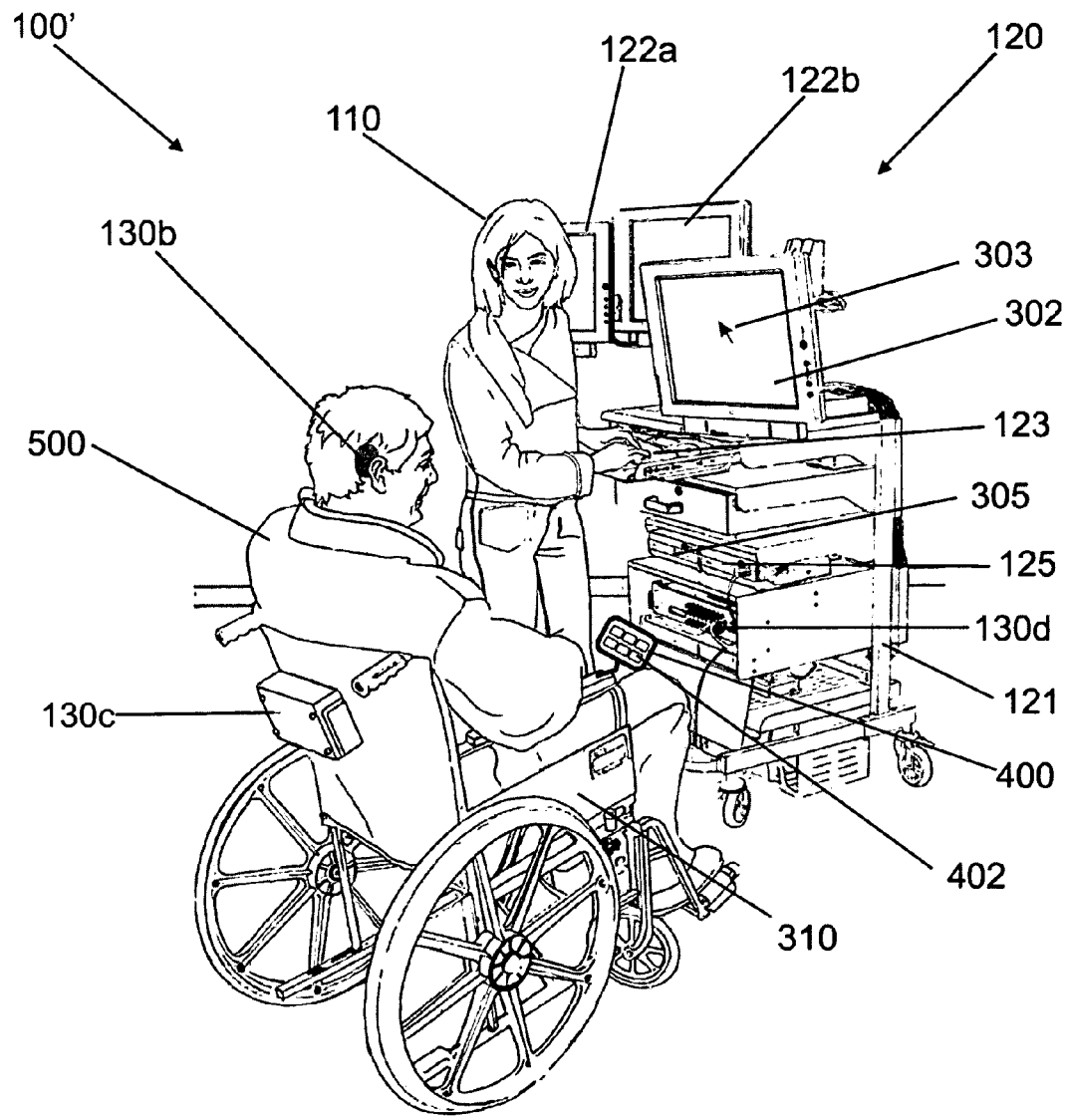
FIG. 3 illustrates another exemplary embodiment of a biological interface system consistent with the present invention wherein an operator configures the system at the patient site.

Referring now to FIG. 3, a biological interface system 100' may comprise implanted components, not shown, and components external to the body of a patient 500. A sensor for detecting multicellular signals, such as a two dimensional array of multiple protruding electrodes, has been implanted in the brain of patient 500, in an area such as the motor cortex. In an exemplary embodiment, the sensor is placed in an area to record multicellular signals that are under voluntary control of the patient. In alternative or addition to the two dimensional array, the sensor may include one or more wires or wire bundles which include a plurality of electrodes. Patient 500 of FIG. 3 is shown as a human being, but other mammals and life forms that produce recordable multicellular signals would also be applicable. Patient 500 may be a patient with a spinal cord injury or afflicted with a neurological disease that has resulted in a loss of voluntary control of various muscles within the patient's body. Alternatively or additionally, patient 500 may have lost a limb, and system 100' may include a prosthetic limb as its controlled device.

The sensor electrodes of system 100' can be used to detect various multicellular signals including neuron spikes, electrocorticogram signals (ECoG), local field potential (LFP) signals, electroencelphalogram (EEG) signals, and other cellular and multicellular signals. The electrodes can detect multicellular signals from clusters of neurons and provide signals midway between single neuron and electroencephalogram recordings. Each electrode is capable of recording a combination of signals, including a plurality of neuron spikes. The sensor can be placed on the surface of the brain without penetrating, such as to detect local field potential (LFP) signals, or on the scalp to detect electroencephalogram (EEG) signals.

A portion of the processing unit, such as processing unit second portion 130b, receives signals from an implanted processing unit component, such as has been described in reference to FIG. 1 and FIG. 2. Processing unit second portion 130b is located just above the ear of patient 500, such that the data transmitting implanted component is located under the scalp in close proximity to the location of processing unit second portion 130b as depicted in FIG. 3. Signals are transmitted from the implanted processing unit component to processing unit second portion 130b using wireless transmission means. The processing unit components of system 100' perform various signal processing functions including but not limited to: amplification, filtering, sorting, conditioning, translating, interpreting, encoding, decoding, combining, extracting, sampling, multiplexing, analog-to-digital converting, digital to analog converting, mathematically transforming, and/or otherwise processing cellular signals to generate a control signal for transmission to a controllable device. The processing unit may process signals that are mathematically combined, such as the combining of neuron spikes that are first separated using spike discrimination methods. In an exemplary embodiment, the processing unit is for using a cellular signal from a neuron whose signal is separated from other nearby neurons. In alternative embodiments, the processing unit may comprise multiple components or a single component. Each of the processing unit components can be fully implanted in patient 500, be external to the body, or be implanted with a portion of the component exiting through the skin.

In FIG. 3, one controlled device is a computer (e.g., CPU 305) that is attached to monitor 302. Through the use of system 100', patient 500 can control cursor 303 of CPU 305 and potentially other functions of the computer such as turning it on and off, keyboard entry, joystick control, or control of another input device, each function individually or in combination. System 100' includes another controlled device, wheelchair 310. Numerous other controlled devices can be included in the systems of this application, individually or in combination, including but not limited to: a computer; a computer display; a mouse; a cursor; a joystick; a personal data assistant; a robot or robotic component; a computer controlled device; a teleoperated device; a communication device or system; a vehicle such as a wheelchair; an adjustable bed; an adjustable chair; a remote controlled device; a Functional Electrical Stimulator device or system; a muscle stimulator; an exoskeletal robot brace; an artificial or prosthetic limb; a vision enhancing device; a vision restoring device; a hearing enhancing device; a hearing restoring device; a movement assist device; medical therapeutic equipment such as a drug delivery apparatus; medical diagnostic equipment such as epilepsy monitoring apparatus; other medical equipment such as a bladder control device, a bowel control device, and a human enhancement device; closed loop medical equipment; and other controllable devices applicable to patients with some form of paralysis or diminished function as well as any device that may be utilized under direct brain or thought control in either a healthy or unhealthy patient.

The sensor is connected via a multi-conductor cable, not shown but implanted in patient 500, to an implanted portion of the processing unit which includes some signal processing elements as well as wireless communication means as has been described in detail in reference to FIG. 1 and FIG. 2. The implanted multi-conductor cable preferably includes a separate conductor for each electrode, as well as additional conductors to serve other purposes, such as providing reference signals and ground.

Processing unit second portion 130b includes various signal processing elements including but not limited to: amplification, filtering, sorting, conditioning, translating, interpreting, encoding, decoding, combining, extracting, sampling, multiplexing, analog-to-digital converting, digital to analog converting, mathematically transforming, and/or otherwise processing cellular signals to generate a control signal for transmission to a controllable device. Processing unit second portion 130b includes a unique electronic identifier, such as a unique serial number or any alphanumeric or other retrievable, identifiable code associated uniquely with the system 100' of patient 500. The unique electronic identifier may take many different forms in processing unit second portion 130b, such as a piece of electronic information stored in a memory module; a semiconductor element or chip that can be read electronically via serial, parallel, or telemetric communication; pins or other conductive parts that can be shorted or otherwise connected to each other or to a controlled impedance, voltage, or ground to create a unique code; pins or other parts that can be masked to create a binary or serial code; combinations of different impedances used to create a serial code that can be read or measured from contacts, features that can be optically scanned and read by patterns and/or colors; mechanical patterns that can be read by mechanical or electrical detection means or by mechanical fit, a radio frequency identifier or other frequency spectral codes sensed by radiofrequency or electromagnetic fields, pads and/or other marking features that may be masked to be included or excluded to represent a serial code, or any other digital or analog code that can be retrieved from the discrete component.

Alternatively or in addition to embedding the unique electronic identifier in processing unit second portion 130b, the unique electronic identifier can be embedded in one or more implanted discrete components. Under certain circumstances, processing unit second portion 130b or another external or implanted component may need to be replaced, temporarily or permanently. Under these circumstances, a system compatibility check between the new component and the remaining system components can be confirmed at the time of the repair or replacement surgery through the use of the embedded unique electronic identifier.

The unique electronic identifier can be embedded in one or more of the discrete components at the time of manufacture, or at a later date such as at the time of any clinical procedure involving the system, such as a surgery to implant the sensor electrodes into the brain of patient 500. Alternatively, the unique electronic identifier may be embedded in one or more of the discrete components at an even later date such as during a system configuration such as a calibration procedure.

Referring again to FIG. 3, processing unit second portion 130b communicates with one or more discrete components of system 100' via wireless communication means. Processing unit second portion 130b communicates with selector module 400, a component utilized to select the specific device to be controlled by the processed signals of system 100'. Selector module 400 includes input element 402 (e.g., a set of buttons) used to perform the selection process. Processing unit second portion 130b also communicates with controlled device CPU 305, such as to control cursor 303 or another function of CPU 305. Processing unit second portion 130b also communicates with processing unit third portion 130c. Processing unit third portion 130c provides additional signal processing functions, as have been described above, to control wheelchair 310. System 100' of FIG. 3 utilizes selector module 400 to select one or more of CPU 305, wheelchair 310 or another controlled device, not shown, to be controlled by the processed signals produced by the processing unit of the present invention. System 100' also includes a modality wherein one set of processed signals emanate from one portion of the processing unit (e.g., processing unit second portion 130b), and a different set of processed signals emanate from a different portion of the processing unit (e.g., processing unit third portion 130c).

The various components of system 100' communicate with wireless transmission means. However, it should be appreciated that physical cables can be used to transfer information alternatively or in addition to wireless means. These physical cables may include electrical wires, optical fibers, sound wave guide conduits, other physical means of transmitting data and/or power, and any combination of those means.

An operator 110, such as a qualified individual, may perform a configuration of system 100' at some time during the use of system 100, preferably soon after implantation of the sensor. In an exemplary embodiment, at least one configuration routine is performed and successfully completed by operator 110 prior to use of system 100' by patient 500. As depicted in FIG. 3, operator 110 utilizes configuration apparatus 120 which includes two monitors (e.g., first configuration monitor 122a and second configuration monitor 122b) configuration keyboard 123, and configuration CPU 125 to perform a calibration routine or other system configuration process such as patient training, algorithm and algorithm parameter selection, and output device setup. The software programs and hardware required to perform the configuration can be included in the processing unit such as processing unit second portion 130b, selector module 400, or configuration apparatus 120. Configuration apparatus 120 may include additional input devices, such as a mouse or joystick, not shown. Configuration apparatus 120 may include various elements, functions, and data including but not limited to: memory storage for future recall of configuration activities; operator qualification routines; standard human data; standard synthesized or artificial data; neuron spike discrimination software; operator security and access control; controlled device data; wireless communication means; remote (such as via the Internet) configuration communication means; and other elements, functions, and data used to provide an effective and efficient configuration on a broad base of applicable patients and a broad base of applicable controlled devices. The unique electronic identifier can be embedded in one or more of the discrete components at the time of system configuration, including the act of identifying a code that was embedded into a particular discrete component at its time of manufacture, and embedding that code in a different discrete component. In an alternative embodiment, all or part of the functionality of configuration apparatus 120 is integrated into selector module 400 such that system 100' can perform one or more configuration processes such as a calibration procedure utilizing selector module 400 without the availability of configuration apparatus 120.

In an exemplary embodiment, an automatic or semi-automatic configuration function or routine is embedded in system 100'. This embedded configuration routine can be used in place of a configuration routine performed manually by Operator 110 as is described hereabove, or can be used in conjunction with one or more manual configurations. Automatic and/or semi-automatic configuration events can take many forms including but not limited to: monitoring of cellular activity, wherein the system automatically changes which particular signals are chosen to produce the processed signals; running parallel algorithms in the background of the one or more algorithms currently used to create the processed signals, and changing one or more algorithms when improved performance is identified in the background event; monitoring of one or more system functions, such as alarm or warning condition events or frequency of events, wherein the automated system shuts down one or more functions and/or improves performance by changing a relevant variable; and other methods that monitor one or more pieces of system data, identify an issue or potential improvement, and determine new parameters that would reduce the issue or achieve an improvement. In an exemplary embodiment of the disclosed invention, when specific integrated parameters are identified, by an automated or semi-automated calibration or other configuration routine, to be modified for the reasons described above, an integral permission routine of the system requires approval of a specific operator when one or more of the integrated parameters is modified. Lists and matrices of operator names, identifiers, passwords, and permissions can be included in system memory of one or more discrete components.

Operator 110 may be a clinician, technician, caregiver, patient family member, or even the patient themselves in some circumstances. Multiple operators may be needed or required to perform a configuration or approve a modification of an integrated parameter, and each operator may be limited by system 100', via passwords and other control configurations, to only perform or access specific functions. For example, only the clinician may be able to change specific critical parameters, or set upper and lower limits on other parameters, while a caregiver, or the patient, may not be able to access those portions of the configuration procedure or the permission procedure. The configuration procedure includes the setting of numerous parameters needed by system 100' to properly control one or more controlled devices. The parameters include but are not limited to various signal conditioning parameters as well as selection and de-selection of specific multicellular signals for processing to generate the device control creating a subset of signals received from the sensor to be processed. The various signal conditioning parameters include, but are not limited to, threshold levels for amplitude sorting, other sorting and pattern recognition parameters, amplification parameters, filter parameters, signal conditioning parameters, signal translating parameters, signal interpreting parameters, signal encoding and decoding parameters, signal combining parameters, signal extracting parameters, mathematical parameters including transformation coefficients and other signal processing parameters used to generate a control signal for transmission to a controlled device.

The configuration routine may result in the setting of various configuration output parameters, all such parameters to be considered integrated parameters of the system of the present invention. Configuration output parameters may include, but be not limited to: electrode selection, cellular signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal, and filter parameters by group of signals. In an exemplary embodiment, the configuration output parameters are stored in memory in one or more discrete components, and the parameters are linked to the system's unique electronic identifier.

Calibration and other configuration routines, including manual, automatic, and semi-automatic routines, may be performed on a periodic basis, and may include the selection and deselection of specific cellular signals over time. The initial configuration routine may include setting initial values, or starting points, for one or more of the configuration output parameters. Setting initial values of specific parameters, may invoke a permission routine. Subsequent configuration routines may involve utilizing previous configuration output parameters that have been stored in a memory storage element of system 100'. Subsequent configuration routines may be shorter in duration than an initial configuration and may require less patient involvement. Subsequent configuration routine results may be compared to previous configuration results, and system 100' may require a repeat of configuration if certain comparative performance is not achieved.

The configuration routine may include: (a) setting a preliminary set of configuration output parameters; (b) generating processed signals to control the controlled device; (c) measuring the performance of the controlled device control; and (d) modifying the configuration output parameters. The configuration routine may further include the steps of repeating steps (b) through (d). The configuration routine may also require invoking the permission routine of the present invention.

In the performance of the configuration routine, the operator 110 may involve patient 500 or perform steps that do not involve the patient. The operator 110 may have patient 500 imagine one or more particular movements, imagined states, or other imagined events, such as a memory, an emotion, the thought of being hot or cold, or other imagined event not necessarily associated with movement. The patient participation may include the use of one or more cues such as audio cues, visual cues, olfactory cues, and tactile cues. The patient 500 may be asked to imagine multiple movements, and the output parameters selected during each movement may be compared to determine an optimal set of output parameters. The imagined movements may include the movement of a part of the body, such as a limb, arm, wrist, finger, shoulder, neck, leg, angle, and toe, and imagining moving to a location, moving at a specific velocity or moving at planned acceleration. The patient may imagine the movement while viewing a video or animation of a person performing the specific movement pattern. In an exemplary embodiment, this visual feedback is shown from the patient's perspective, such as a video taken from the person performing the motion's own eye level and directional view. Multiple motion patterns and multiple corresponding videos may be available to improve or otherwise enhance the configuration process. The configuration routine correlates the selected movement with modulations in the multicellular signals received from the sensor, such as by correlating the periodicity of the movement with a periodicity found in one or more cellular signals. Correlations can be based on numerous variables of the motion including but not limited to position, velocity, and acceleration.

The configuration routine may utilize one or more configuration input parameters to determine the configuration output parameters. In addition to the multicellular signals themselves, system or controlled device performance criteria can be utilized. Other configuration input parameters include various properties associated with the multicellular signals including one or more of: signal to noise ratio, frequency of signal, amplitude of signal, neuron firing rate, average neuron firing rate, standard deviation in neuron firing rate, modulation of neuron firing rate as well as a mathematical analysis of any signal property including but not limited to modulation of any signal property. Additional configuration input parameters include but are not limited to: system performance criteria, controlled device electrical time constants, controlled device mechanical time constants, other controlled device criteria, types of electrodes, number of electrodes, patient activity during configuration, target number of signals required, patient disease state, patient condition, patient age and other patient parameters, and event based (such as a patient imagined movement event) variations in signal properties including neuron firing rate activity. In an exemplary embodiment, one or more configuration input parameters are stored in memory and linked to the embedded, specific, unique electronic identifier. All configuration input parameters shall be considered an integrated parameter of the system of the present invention.

It may be desirous for the configuration routine to exclude one or more multicellular signals based on a desire to avoid signals that respond to certain patient active functions, such as non-paralyzed functions, or even certain imagined states. The configuration routine may include having the patient imagine a particular movement or state, and based on sufficient signal activity such as firing rate or modulation of firing rate, exclude that signal from the signal processing based on that particular undesired imagined movement or imagined state. Alternatively real movement accomplished by the patient may also be utilized to exclude certain multicellular signals emanating from specific electrodes of the sensor. In an exemplary embodiment, an automated or semi-automated calibration or other configuration routine may include through addition, or exclude through deletion, a signal based on insufficient activity during known patient movements.

Patient 500 of FIG. 3 can be a quadriplegic, a paraplegic, an amputee, a spinal cord injury victim, or a physically impaired person. Alternatively or in addition, patient 500 may have been diagnosed with one or more of: obesity, an eating disorder, a neurological disorder, a psychiatric disorder, a cardiovascular disorder, an endocrine disorder, sexual dysfunction, incontinence, a hearing disorder, a visual disorder, sleeping disorder, a movement disorder, a speech disorder, physical injury, migraine headaches, or chronic pain. System 100' can be used to treat one or more medical conditions of patient 500, or to restore, partially restore, replace or partially replace a lost function of patient 500. Lost functions can include but are not limited to: vision, hearing, speech, communication, limb motion, limb motion, ambulation, reaching, grasping, standing, rolling over, bowel movement, and bladder evacuation.

Alternatively, system 100' can be utilized by patient 500 to enhance performance, such as if patient 500 did not have a disease or condition from which a therapy or restorative device could provide benefit, but did have an occupation wherein thought control of a device provided an otherwise unachieved advancement in healthcare, crisis management, and national defense. Thought control of a device can be advantageous in numerous healthy individuals including but not limited to: a surgeon, such as an individual surgeon using thought control to maneuver three or more robotic arms in a complex laparoscopic procedure; a crisis control expert, such as a person who in attempting to minimize death and injury uses thought control to communicate different pieces of information and/or control multiple pieces of equipment, such as urban search and rescue equipment, simultaneously during an event such as an earthquake or other disaster, both natural disasters and those caused by man; a member of a bomb squad, such as an expert who uses thoughts to control multiple robots and/or robotic arms to remotely diffuse a bomb; and military personnel who use thought control to communicate with personnel and control multiple pieces of defense equipment, such as artillery, aircraft, watercraft, land vehicles and reconnaissance robots. It should be noted that the above advantages of system 100' to a healthy individual are also advantages achieved in a patient such as a quadriplegic or paraplegic. In other words, a quadriplegic could provide significant benefit to society, such as in controlling multiple bomb diffusing robots, in addition to his or her own ambulation and other quality of life devices. Patients undergoing implantation and use of the system 100' of the present invention may provide numerous occupational and other functions not available to individuals that do not have the biological interface system of the present invention.

The systems of the present invention, such as system 100' of FIG. 3, include a processing unit that processes multicellular signals received from patient 500. Processing unit second portion 130b and other processing unit components, singly or in combination, perform one or more functions. The functions performed by the processing unit include but are not limited to: producing the processed signals; transferring information to a separate device; receiving information from a separate device; producing processed signals for a second controlled device; activating an alarm, alert or warning; shutting down a part of or the entire system; ceasing control of a controlled device; storing information and performing a configuration.

In order for the processing unit of system 100' to perform one or more functions, one or more integrated parameters are utilized. These parameters include pieces of information stored in, sent to, or received from, any component of system 100, including but not limited to: the sensor; a processing unit component; processing unit second portion 130b; or a controlled device. Parameters can be received from devices outside of system 100' as well, such as configuration apparatus 120, a separate medical therapeutic or diagnostic device, a separate Internet based device or a separate wireless device. These parameters can be numeric or alphanumeric information, and can change over time, either automatically or through an operator involved configuration or other procedure.

In order to change an integrated parameter, system 100' includes a permission routine, such as an embedded software routine or software driven interface that allows the operator to view information and enter data into one or more components of system 100. The data entered must signify an approval of the parameter modification in order for the modification to take place. Alternatively, the permission routine may be partially or fully located in a separate device such as configuration apparatus 120 of FIG. 3, or a remote computer such as a computer that accesses system 100' via the Internet or utilizing wireless technologies. In order to access the permission routine, and/or approve the modification of the integrated parameters, a password or security key, either mechanical, electrical, electromechanical or software based, may be required of the operator. Multiple operators may be needed or required to approve a parameter modification. Each specific operator or operator type may be limited by system 100', via passwords and other control configurations, to approve the modification of only a portion of the total set of modifiable parameters of the system. Additionally or alternatively, a specific operator or operator type may be limited to only approve a modification to a parameter within a specific range of values, such as a range of values set by a clinician when the operator is a family member. Operator or operator types, hereinafter operator, include but are not limited to: a clinician, primary care clinician, surgeon, hospital technician, system 100' supplier or manufacturer technician, computer technician, family member, immediate family member, caregiver and patient.

Figure 4:
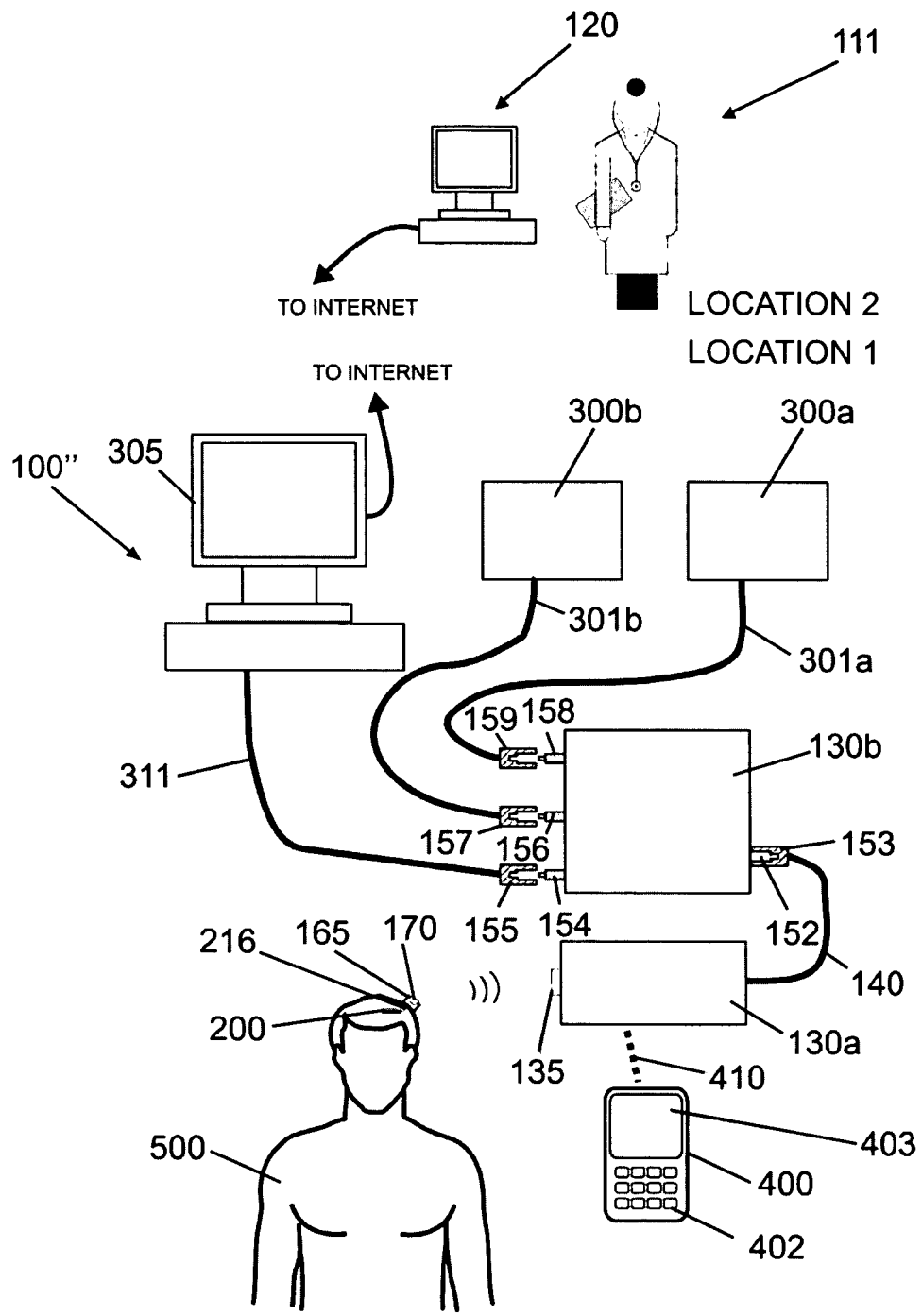
FIG. 4 illustrates another exemplary embodiment of a biological interface system consistent with the present invention wherein a patient controls multiple devices and an operator configures the system at a site remote from the patient.

Referring now to FIG. 4, a biological interface system 100" may comprise implanted components and components external to the body of patient 500. System 100" includes multiple controlled devices. For example, the system 100" may comprise controlled computer 305, first controlled device 300a and second controlled device 300b. While three controlled devices are depicted, the system 100" may include any configuration of two or more controlled devices for a single patient. First controlled device 300a and second controlled device 300b can include various types of devices such as prosthetic limbs or limb assist devices, robots or robotic devices, communication devices, computers and other controllable devices as have been described in more detail hereinabove. The multiple controlled devices can include two or more joysticks or simulated joystick interfaces, two or more computers, a robot and another controlled device, and many other combinations and multiples of devices as have been described in detail hereabove. Each controlled device is one or more discrete components of the present invention, or a portion of a discrete component.

A sensor 200 for detecting multicellular signals, and preferably a two dimensional array of multiple protruding electrodes, has been implanted in the brain of patient 500, in an area such as the motor cortex. In an exemplary embodiment, the sensor 200 is placed in an area to record multicellular signals that are under voluntary control of the patient. Alternatively or additionally, the sensor may include an additional array; one or more wires or wire bundles which include a plurality of electrodes; subdural grids; cuff electrodes; scalp electrodes; or other single or multiple electrode configurations. Sensor 200 is attached to transcutaneous connector 165 via wiring 216 (e.g., a multi-conductor cable) that preferably, though not necessarily, includes a separate conductor for each electrode of sensor 200. Transcutaneous connector 165 includes a pedestal which is attached to the skull of the patient such as with glues and/or bone screws, preferably in the same surgical procedure in which sensor 200 is implanted in the brain of patient 500. Electronic module 170 attaches to transcutaneous connector 165 via threads, bayonet lock, magnetic coupling, Velcro, or any other engagement means. Transcutaneous connector 165 and/or electronic module 170 may include integrated electronics including but not limited to signal amplifier circuitry, signal filtration circuitry, signal multiplexing circuitry, and other signal processing circuitry, such that transcutaneous connector 165 and/or electronic module 170 provide at least a portion of the processing unit of the disclosed invention. Transcutaneous connector 165 preferably includes electrostatic discharge protection circuitry. Electronic module 170 includes wireless information transfer circuitry, utilizing one or more of radiofrequency, infrared, ultrasound, microwave or other wireless communication means. In an alternative embodiment, transcutaneous connector 165 includes all the appropriate electronic signal processing, electrostatic discharge protection circuitry, and other circuitry, and also includes wireless transmission means, such that the need for electronic module 170 is obviated.

In an exemplary embodiment, electronic module 170 includes wireless transmission means and a power supply, not shown, such that as the power supply is depleted or electronic module 170 has a malfunction, it can be easily replaced. In another exemplary embodiment, electronic module 170 is a disposable component of system 100". Electronic module 170 transmits information to processing unit transceiver 135 which is integrated into a portion of system 100"s processing unit, processing unit first portion 130a. In an exemplary embodiment, processing unit transceiver 135 is a two-way wireless communication device and electronic module 170 is also a two-way wireless communication device such that information can be sent to or from electronic module 170.

All of the physical cables of FIG. 4, as well as all the other figures of this disclosure, can be in a permanently attached, or in a detachable form. In addition, all of the physical cables included in system 100" of FIG. 4 as well as the systems of the other included figures can be eliminated with the inclusion of wireless transceiver means incorporated into the applicable, communicating discrete components. Processing unit first portion 130a, a discrete component as defined in this disclosure, includes various signal processing functions as has been described in detail in relation to separate figures hereabove. Processing unit first portion 130a preferably includes a unique system identifier, the makeup and applicability of the unique identifier also described in detail hereabove. Processing unit first portion 130a electrically connects to processing unit second portion 130b via intra-processing unit cable 140. Cable 140 is detachable from processing unit second portion 130b via female plug 153 which is attached to processing unit second portion 130b at its input port, male receptacle 152. Cable 140 may be constructed of electrical wires and/or fiber optic cables. In an exemplary embodiment, data is transmitted from processing unit first portion 130a to processing unit second portion 130b via a fiber optic cable. Information and other signals transmitted between processing unit first portion 130a and processing unit second portion 130b may be in analog format, digital format, or a combination of both. In addition, wireless transmission of information can be provided, not shown, to replace intraprocessing unit cable 140 or work in conjunction with intraprocessing unit cable 140.

Processing unit second portion 130b includes further signal processing means which in combination with the signal processing of processing unit first portion 130a produces processed signals, such as to control multiple controlled devices. Processing unit first portion 130a and/or processing unit second portion 130b include various functions including but not limited to: a spike sorting function, such as a threshold based neuron spike sorting function; an amplifier function; a signal filtering function; a neural net software function; a mathematical signal combination function; a neuron signal separation function such as a spike discrimination function or a minimum amplitude sorting function; and a database storage and retrieval function such as a database including a list of acceptable neural information or a database of unacceptable neural information each of which can be used to perform a system diagnostic. In another exemplary embodiment, the processing unit assigns one or more cellular signals to a specific use, such as a specific use that is correlated to a patient imagined event.

The processed signals emanating from processed unit second portion 130b can be analog signals, digital signals, or a combination of analog and digital. The processing unit of the present invention may include digital-to-analog conversion means as well as analog-to-digital conversion means. The processed signals can be transmitted to one or more controlled devices with a hardwired connection, a wireless connection or a combination of both technologies. As depicted in FIG. 4, controlled computer 305, first controlled device 300a, and second controlled device 300b are controlled by the processed signals produced by processing unit first portion 130a and processing unit second portion 130b. Similar to processing unit first portion 130a, processing unit second portion 130b preferably includes the system unique electronic identifier, which can be embedded in processing unit second portion 130b at the time of manufacture, during installation procedures, during calibration or other post-surgical configuration procedures, or at a later date.

The three controlled devices are shown permanently attached to physical cables, with each physical cable including a removable connection at the other end. Controlled computer 305 is attached to cable 311 that has female plug 155 at its end. First controlled device 300a is attached to first controlled device cable 301a which has female plug 159 at its end. Second controlled device 300b is attached to second controlled device cable 301b which has female plug 157 at its end. Each physical cable can be attached and detached from processing unit second portion 130b. Female plug 159 attaches to male receptacle 158; female plug 157 attaches to male receptacle 156; and female plug 155 attaches to male receptacle 154.

Each of controlled computer 305, first controlled device 300a, and second controlled device 300b preferably has embedded within it, a unique identifier of the particular device. Additional codes, such as the unique system identifier, may also be embedded. When any of the physical cables are first attached, such as controlled computer cable 311 being attached via female plug 157 to male receptacle 156, a compatibility check is performed by system 100" to assure that the unique system identifier embedded in controlled computer 305 is identical or otherwise compatible with a unique electronic identifier embedded in any and all other discrete components of system 100", such as the unique electronic identifier embedded in processing unit second portion 130b. Similar system compatibility checks can be performed with the attachment of first controlled device 300a or second controlled device 300b. If improper compatibility is determined by system 100", various actions that can be taken include but are not limited to: entering an alarm state, displaying incompatibility information, transmitting incompatibility information, deactivation of controlled device control, limiting controlled device control and other actions.

Also depicted in FIG. 4 is selector module 400 which can be used by the patient or a different operator, such as a clinician, to select one or more specific devices to be controlled by the processed signals of system 100". Selector module 400 includes numerous elements and functional capability as has been described in detail in relation to FIG. 1. Selector module 400 is shown with input element 402 (e.g., a data entry keypad) and output element 403 (e.g., a visual display). Input element 402 is used by an operator to select the specific controlled device and to perform other data entry. Output element 403 provides information to the operator such as selectable controlled device icons, controlled device information and other system information. Selector module 400 communicates with processing unit first portion 130a via wireless technology 410. After selection of the one or more controlled devices to be controlled by the processed signals, these processed signals include one or more unique codes identifying the selected controlled device or devices, and may additionally include the unique system identifier. These codes can be sent at the initiation or cessation of control or on a periodic or continuous basis in order to assure that only the selected devices are controlled by the processed signals. A selection event can either cause a controlled device to begin to be controlled or stop the control of a controlled device that is already being controlled. In an exemplary embodiment, specific operators can select specific equipment, such conditional matrix stored in a memory module of selector module 400 or other discrete component of system 100".

Selector module 400 may include access passwords, or require mechanical or electronic keys to prevent unauthorized use, and may also include a function, such as a permission routine function, to select a controlled device to modify its control. Selector module 400 may have other integrated functions such as information recall functions, system configuration or calibration functions as well as a calculator, cellular telephone, pager or personal data assistant (PDA) functions. Clinician control unit 400 may be a PDA that has been modified to access system 100" to select one or more controlled device to modify its control, such as through the use of a permission routine.

Selector module 400 of FIG. 4 includes an integrated monitor for displaying the information, however in an alternative embodiment, the selector module 400 can cause the information to be displayed on a separate visualization apparatus such as the monitor of controlled computer 305. Alternatively or additionally, one or more of the functions of the selector module 400 can be integrated into one or more discrete components of system 100".

Numerous configurations and types of controlled devices can be used with system 100" of FIG. 4. Numerous types of controlled devices have been described in detail in relation to the systems of FIG. 1 and FIG. 3 and are applicable to system 100" of FIG. 4 as well. System 100" works with a single patient 500 who can control multiple controlled devices such as controlled computer 305, first controlled device 300a, and second controlled device 300b. In an exemplary embodiment, patient 500 can select and/or control more than one controlled device simultaneously. While each controlled device is connected to the same discrete component, such as processing unit second portion 130b, in an alternative embodiment, the multiple controlled devices can be connected to multiple processing unit discrete components. In that embodiment, the selector module 400 is used to start or stop the transmission of the individual processing units to their corresponding controlled device.

While patient 500 has been implanted with a sensor 200 comprising a single discrete component, sensor 200 may comprise multiple discrete components, not shown, such as multiple electrode arrays, implanted in different parts of the brain, or in other various patient locations to detect multicellular signals. Cellular signals from the individual sensor discrete components, such as a single electrode component, may be sent to individual processing units, or to a single processing unit. Separate processed signals can be created from each individual discrete component of the sensor, and those particular signals tied to a specific controlled device. Thus, each controlled device can be controlled by processed signals from a different sensor discrete assembly, such as discrete components at different locations in the brain or other parts of the body. It should be appreciated that any combination of discrete component cellular signals can be used in any combination of multiple controlled devices. Alternatively, whether the sensor is embodied in a single discrete component or multiple discrete components, the processed signals for individual controlled devices may be based on specific cellular signals or signals from specific electrodes, such that individual device control is driven by specific cellular signals. Any combination of exclusively assigned cellular signals and shared cellular signals used to create processed signals for multiple controlled devices are to be considered within the scope of this application. In an alternative embodiment, the system includes multiple patients collectively selecting and/or controlling one or more controlled devices.

The system 100" of FIG. 4 may include two or more separate configuration routines, such as a separate calibration routine for each controlled device. Any and all discrete components of system 100" may have a unique electronic identifier embedded in it. The processing unit of system 100", comprising processing unit first portion 130a and processing unit second portion 130b, may conduct adaptive processing as has been described hereabove.

The unique electronic identifier of the system is a unique code used to differentiate one system, such as the system of a single patient, from another system, as well as differentiate all discrete components of a system, especially detachable components, from discrete components of a separate, potentially incompatible system. The unique electronic identifier may be a random alphanumeric code, or may include information including but not limited to: patient name, other patient information, system information, implant information, number of electrodes implanted, implant location or locations, software revisions of one or more discrete components, clinician name, date of implant, date of calibration, calibration information, manufacturing codes, and hospital name. In an exemplary embodiment, the unique electronic identifier is stored in more than one discrete component such as a sensor discrete component and a processing unit discrete component. The unique electronic identifier may be programmable, such as one time programmable, or allow modifications for multiple time programming, such programming performed in the manufacturing of the particular discrete component, or by a user at a later date. The unique electronic identifier may be configured to be changed over time, such as after a calibration procedure. The unique electronic identifier can be permanent or semi-permanent, or hard-wired, such as a hard-wired configuration in a transcutaneous connector of the system. The unique electronic identifier can be used in wireless communications between discrete components, or in wireless communications between one or more discrete components and a device outside of the system. The unique electronic identifier can represent or be linked to system status. System status can include but not be limited to output signal characteristics, level of accuracy of output signal, output signal requirements, level of control needed, patient login settings, such as customized computer configuration information, one or more software revisions, one or more hardware revisions, controlled device compatibility list, patient permissions lists, and calibration status. In an exemplary embodiment, the unique identifier includes information to identify the system as a whole, as well as information identifying each discrete component, such as each controlled device applicable to the system. The unique portion identifying each controlled device can be used in wireless communication, after a selection has been made via the selector module, such that the selected controlled devices are properly controlled.

The system 100" of FIG. 4 may include a library of various integrated parameters, such integrated parameters utilized by the processing units (e.g., processing unit first portion 130*a* and processing unit second portion 130*b*) to perform a function including but not limited to the creation of the processed signals to control one or more controlled devices. Integrated parameters include various pieces of system data, such as data stored in electronic memory. In an exemplary embodiment, the data being electronically linked with the unique electronic identifier of system 100". The integrated parameter data may be stored in memory of one or more discrete components, such as processing unit second portion 130*b*. Alternatively or additionally, the integrated parameter data may be stored in a computer based network platform, separate from system 100' such as a local area network (LAN), a wide area network (WAN) or the Internet. The integrated parameter data can contain numerous categories of information related to the system including but not limited to: patient information such as patient name and disease state; discrete component information such as type of sensor and electrode configuration; system configuration information such as calibration dates, calibration output parameters, calibration input parameters, patient training data, signal processing methods, algorithms and associated variables, controlled device information such as controlled device use parameters and lists of controlled devices configured for use with or otherwise compatible with the system; and other system parameters useful in using, configuring, and assuring safe and efficacious performance of system 100".

In an alternative embodiment, system 100" of FIG. 4 further comprises a patient feedback module. The feedback module may include one or more of an audio transducer, a tactile transducer, and a visual display. This patient feedback module may be used during patient training, or at all times that the patient is controlling an external device. Feedback can be used to enhance external device control as well as avoid an unsafe or undesirable condition. The feedback module may utilize one or more discrete components of system 100" such as sensor 200. In another exemplary embodiment, one or more electrodes of sensor 200 can be stimulated, such as via a stimulation circuit provided by one or more of transcutaneous connector 165 or electronic module 170. The stimulation can evoke a variety of responses including but not limited to the twitching of a patient's finger. The feedback signal sent to the patient can take on a variety of forms, but is preferably a derivative of a modulating variable of the controlled device. For example, feedback can be a derivative of cursor position of controlled computer 305. If audio feedback is implemented, a signal representing horizontal position and a signal representing vertical position can be combined and sent to a standard speaker. Other audio feedback, such as specific discrete sounds, can be incorporated to represent proximity to an icon, etc. Parameters of the feedback module should be considered integrated parameters of the systems of this invention, such that one or more feedback parameters require approval of an operator via the system's permission routine. In an exemplary embodiment, the patient feedback function is incorporated into selector module 400 such as via a visual display or audio transducer.

Patient 500 of FIG. 4 is at a specific location, Location 1. An operator such as a clinician operator 111 is at a location remote from patient 500, Location 2. Also at Location 2 is configuration system 120 that can access system 100" via the Internet as has been described in reference to previous embodiments of the present invention. Configuration system 120 can be used to perform various configuration procedures such as calibration procedures as has been described in reference to a similar configuration system of FIG. 3. In an exemplary embodiment, configuration system 120 can perform the functions of the selector module such that clinician operator 111 can select a specific device to modify its control via configuration apparatus 120 and the Internet.

Figure 5:
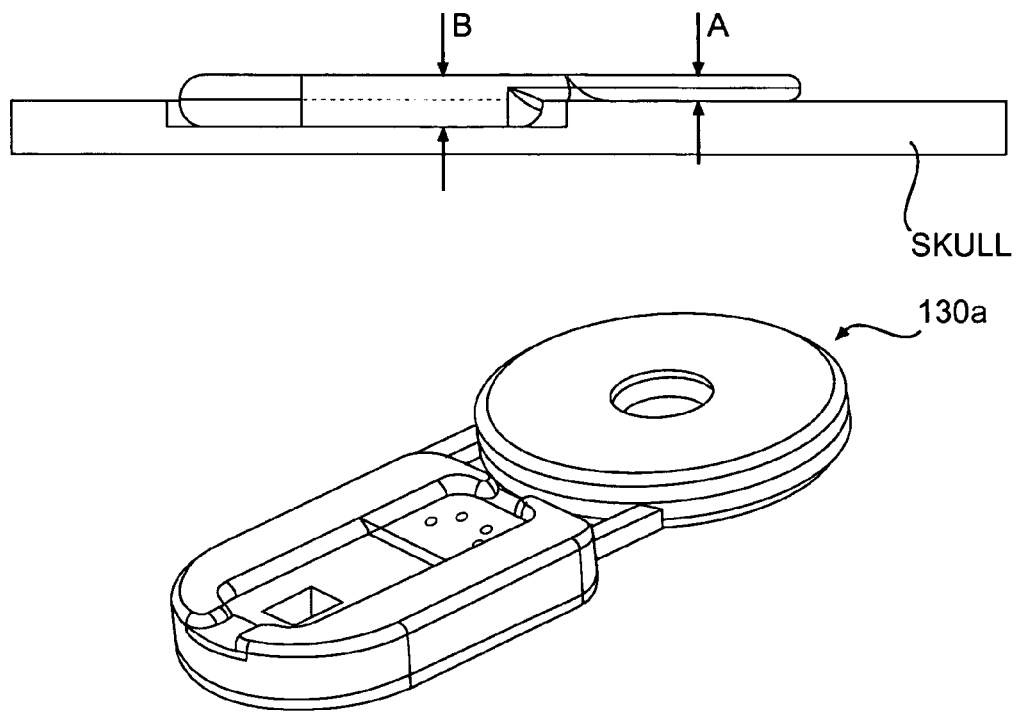
FIG. 5 illustrates another exemplary embodiment of a portion of the biological system including an implanted portion of a processing unit consistent with the present invention.

Referring now to FIG. 5, an implantable processing unit portion (e.g., processing unit first portion 130*a*) is depicted. The sensor and its connection to processing unit first portion 130*a* are not shown. Individuals with severe motor impairments often have intact brain function but are unable to move due to injury or disease of the spinal cord, nerves, or muscles. The embodiments of this application provides a chronic solution for patients with severe motor impairments by advancing technology that is directly applicable to the development of a transcutaneous neural prosthetic BCI. The advanced BCI may significantly increase the independence of severely motor impaired individuals by providing them with safe, long-term, reliable and fast control of a personal computer using thought alone. Through a computer, users could complete daily tasks such as compose an email, answer the telephone, drive their wheelchair, direct medical devices to power their own limbs or carry out other functions that the body is no longer able to perform autonomously or on command—such as bladder/bowel control. The proposed technology may also be leveraged in fields beyond assisting the disabled by providing a safe, chronic tool for real-time analysis of neurophysiological events. This not only evolves the understanding of neuroscience, but also furthers the monitoring and treatment of multiple neurological disorders such as epilepsy or depression.

A functional BCI comprises three distinct modules with sophisticated connectors. These modules include, (i) a data acquisition and transport module, (ii) a data interpretation module, and (iii) at least one data output module. The purpose of a data acquisition module is to extract electrical signals from the brain with sufficient bandwidth and at a favorable signal-to-noise ratio. Early pre-amplification and digitization of the analog recording data is often performed to increase noise immunity and minimize signal deterioration. From the recording site, signals are fed into a processing unit for interpretation. The main goal of the interpretation module is to transform the digitized brain signal into a code which best represents the desired action. For a motor prosthetic this may be movement of a cursor on a computer screen. Though multiple mathematical models currently exist for the interpretation and decoding of intent, better models can be constructed with more clinical experience, as the accuracy of decoding can be augmented through patient feedback. After the data set is interpreted, it can be used to drive a variety of output devices which become the "effector organ" in lieu of muscle-activated limbs. The ability to control a computer cursor is one example of an output device.

Though the technology is in its nascent stages, BCIs have been used to control a computer cursor. In one study, a pair of electrodes was implanted in the primary motor cortex of patients with locked-in syndrome and this led to the ability of some patients to control a computer cursor to communicate. While useful, this system was slow, cumbersome, and unable to be explanted. For these reasons, it is not optimal for widespread use. In another study supported by the FDA and sponsored by applicant, the first implanted patient was able to control a computer cursor without reported difficulty or significant level of concentration. Moreover, and possibly most significant, the patient began communicating through the interface with no training. To date, the patient has cortically played video games, turned his television on and off, changed channels and adjusted the volume.

Though limited to one patient as of September 2004, the applicant's clinical experience with our BCI is groundbreaking neuroscience. However, as it exists today, the technology is limited in both its clinical utility and the number of individuals who can benefit from it. While enhancements to each module of the BCI may have value, the embodiments of this application may specifically utilize best practices in existing technologies with our human clinical experience to develop an enhanced data acquisition and transport module. To date, collecting multi-cellular action potentials from the cortex has partly been hindered for two interrelated reasons. First, there has been a lack of an adequate physical neural interface. Second, there are significant technological limitations in transferring and processing large amounts of data from cerebral cortex. Creating an advanced data acquisition and transport module may provide a chronic device useful for additional clinical study that could further our understanding of the structure and function of the brain and ultimately result in its potential use in many people for multiple indications. Further enhancements such as miniaturization may be necessary to place devices in the confines of the skull; small, high density connectors may be essential to interconnect components, and wireless telemetry may be needed to move signals to remote processors.

Devices intended for long-term monitoring of neural signals from the cerebral cortex are being developed in two broad categories. The first category comprises a passive, micro-electrode array which records signals from the cortex and transports them through a wire bundle to a "can" which amplifies the signals and wirelessly transmits them to an external device located behind the ear. The second is an all-in-one method in which the electrodes, amplifier and wireless data transmission are integrated onto a single substrate that is intended to be implanted on the cortex. In designing a medical device for widespread usage, practical surgical and clinical needs must be taken into account. This application details multiple embodiments: the creation an optimal neural interface to extract reliable and repeatable signals from precisely relevant areas of cortex; a complete, wireless device to transcutaneously transmit neural signals from the cortex to the extracorporeal environment without the need for a through-the-skin connector, and the advanced tools and techniques for a minimally invasive implantation.

Creating an optimal neural interface to extract reliable and repeatable signals from precisely relevant areas of cortex is disclosed. Clinical experience indicates that electrodes must be inserted at a precise depth to ensure recording of the cortical layer with a high signal to noise ratio. The placement of the active tip must take into account both the variability of lamina thickness and the unavoidable range of implant depths occurring during surgery. Some designs use an electrode with multiple active sites along its shank or projection, while others have electrodes only at the tip of the projection.

Sensors which are permanently attached to the processing unit ensures that failure of any implanted component may require the patient to undergo another craniotomy to remove or replace the device. A detachable connector or system wherein a preattached cable can have a connector added to it, obviate the need for the second craniotomy.

The wireless device to transcutaneously transmit neural signals from the cortex to the extracorporeal environment without the need for a through-the-skin connector provides significant advantages. From the cochlear implant experience, it was determined that hardware optimization and algorithm development may require access to all available information. For implants that monitor multiple channels of action potentials, this generally means huge amounts (over 40 Mbits per second) of acquired data. Given foreseeable technology coupled with the competing goal of cosmetic acceptability, high-bandwidth wireless telemetry based on infra-red (IR) transmission is a compelling way to satisfy these competing requirements.

The techniques and approaches embodied in this application may allow minimally invasive implantation for shorter surgical time, less patient scarring, lower risk of infection and faster patient recovery. These embodiments include a new insertion device, surgical templates to aid in proper array placement and tunneling tools to minimize the incision.

Processing unit first portion 130a (e.g., electronics "can") of FIG. 5 attaches to a long-term chronic sensor for the brain and captures neural signals and wirelessly transports them extracorporeally. The sensor comprises an implanted microarray and wire bundle that may be tunneled under the scalp. The wire bundle unit has a sophisticated detachable connector to adjoin with the electronic processing unit implanted under the scalp behind the ear. The processing unit electronics amplify and digitize the signal and then transmits it by, for example, an infrared (IR) telemetry link to a magnetically mounted and aligned external receiver which powers the device using radio-frequency (RF). In the BCI, signals may be forwarded from the receiver to a signal processor and decoder for interpretation.

A microarray of electrodes with a greater range of electrode height, pitch, and shape profile may improve applicability by increasing the number and quality of neural signals obtainable. A flexible and bio-stable cable linking the array and the subcutaneous electronics package is another embodiment. This may vastly improve ease of implantation for the surgeon and lengthen the mean time before failure. A cable connector that allows the subcutaneous electronics "can," a portion of the processing unit of the present invention, to be disconnected and replaced if needed, leaving the microarray/cable intact in the cortex, avoids unnecessary surgery. In an alternative embodiment, a preattached system is implanted that includes a connector addition kit employing a severing device for cutting the wire bundle or ribbon cable used, a connector configured to make electrical connection with each of the conductors at or near the cut end, and a crimping tool for attaching the connector to the conduit. Another embodiment of this application is an electrode array inserter comprising a hold/release mechanism, an inserter mechanism, and a trigger mechanism for safe, easy, repeatable and reliable implantation. Another embodiment is a surgical method utilizing templates and tunneling tools to lessen infection risk, minimize training required, and permit fewer user errors and device damage.

Figure 6:
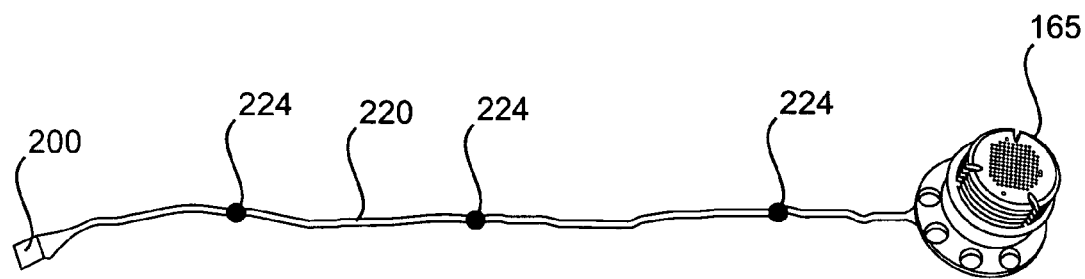
FIG. 6 illustrates another exemplary embodiment of a portion of the biological system including a sensor and a through-the-skin connector for mounting on the skull, consistent with the present invention.

Referring now to FIG. 6, sensor 200 is shown, preferably a ten by ten array of electrodes. Each electrode may be electrically connected to a filamentous conductor, such as a wire, which at their opposite ends is connected to transcutaneous connector 165. The bundle of wires make up wire bundle 220 that includes multiple bound sections (e.g., fixation points 224), which maintain the bundle of wires within a fixed diameter. The portions of wire between each fixation point 224 can flex independently when wire bundle 220 is bent, making wire bundle 220 more flexible than a wire bundle completely surrounded along its length by a protective cap such as a layer of silicone, or a sleeve. Fixation points 224 may comprise a biocompatible band, such as an elastomer band, or an amount of glue holding the cross section of each wire at a fixed position. In an exemplary embodiment, the fixation points are at a predetermined pattern such as an equidistant separation pattern.

Figure 7A:
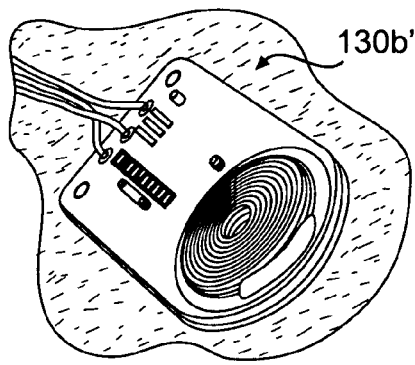
FIG. 7A illustrates another exemplary embodiment of a portion of the biological system including an external portion of the processing unit consistent with the present invention.
Figure 7B:
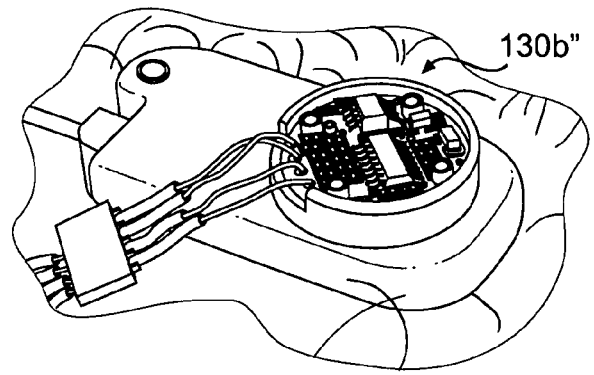
FIG. 7B illustrates another exemplary embodiment of a portion of the biological system including an external portion of the processing unit consistent with the present invention.

FIG. 7A depicts processing unit second portion 130$b'$ of a RF power coil verification prototype placed on a hairless mini-pig. Confirmation of adequate power transmission to an implanted module was confirmed through five millimeters of pig skin. FIG. 7B depicts processing unit second portion 130$b''$ of a wireless telemetry prototype. Accurate, high baud rate (40 Mbit/sec) data transmission to an implanted module was also confirmed. IR alignment tolerance was shown to be better than ±2 mm in x, y, and z axes. Power requirements were less than 40 mW of power. The external processing unit portion of the present invention is configured to inductively transmit power to the implanted processing unit first portion. The implanted processing unit portion includes a sophisticated amplifier for amplifying the multicellular information.

A preferred design of the amplifier has the following specifications:

| Parameter | Specification |
| --- | --- |
| Supply voltage | ±1.5-1.7 V |
| Supply current | ≤±20 μA |
| Gain | 100 +/− 5% |
| Bandwidth (1$^{st}$ order) | 5.7-8.6 kHz |
| Low frequency cutoff | ≤0.2 Hz |
| Input-referred noise | ≤3.0 μVrms |
| Noise efficiency factor | ≤5.0 |
| Dynamic range (%1 THD) | ≥60 dB |
| CMRR(10 Hz-5 kHz) | ≥80 dB |
| PSRR (10 Hz-5 kHz) | ≥80 dB |
| Crosstalk (f = 1 kHz) | ≤−60 dB |
| Offset rejection | Rail to rail |

Figure 8:
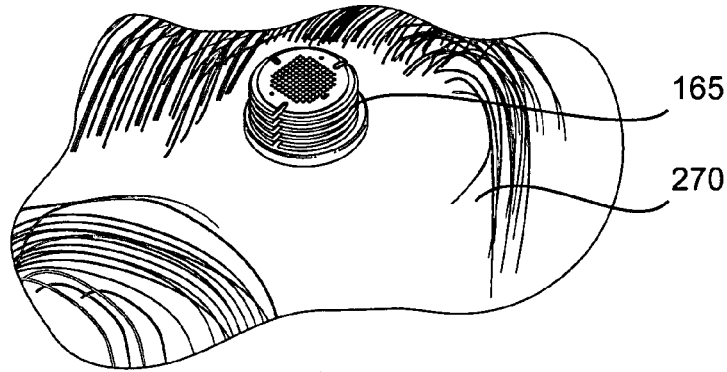
FIG. 8 illustrates another exemplary embodiment of a portion of the biological system including a through-the-skin connector mounted to the skull of a patient consistent with the present invention.

Referring now to FIG. 8, a patient's scalp 270 with transcutaneous connector 165 protruding through the skin is depicted. An incision scar of about 8 cm may be required to place the wire bundle. The microelectrode array was implanted on the surface of the cortex, specifically in the precentral gyrus immediately posterior to the superior frontal sulcus, as identified on a pre-surgical magnetic resonance image (MRI) scan. The array was placed in this area of the motor cortex because it may be the location primarily responsible for motor control of the contralateral hand and arm. Attached to the array, the wire bundle was placed above the skull while the titanium through-the-skin connector was mounted with bone screws to the skull. In an embodiment, a totally integrated subcutaneous package that includes wireless data transmission, ASIC amplifier, and extended safety measures, powered by an RF inductive coil is disclosed.

The surgery lasted approximately three hours and was uneventful. The patient was discharged to his primary residence 3 days post-surgery where he recovered for three weeks prior to initiation of device testing. There were no post-surgical complications. Another embodiment of the present invention addresses the need for immediate feedback during the surgical procedure to ensure the array and connections are in working order. An impedance check, integrated into the implanted signal processing electronics would check the system from the implanted processing unit to the tip of the array before the craniotomy is closed. Based on statistics from deep-brain stimulator and cochlear implant manufacturers, one would expect approximately 3-5% of the implanted electronic "cans" to fail within 5 years. The connector system of the present invention allows the "can" to be replaced without the need for another craniotomy.

Device testing began on Jul. 12, 2004 and continues. As of Oct. 1, 2004, over 20 clinical sessions have been conducted. The current clinical version of the biological interface system is configured with multiple wired connections. An embodiment of the present invention addresses the development of a transcutaneous wireless implant that replaces the head mounted pedestal, preamplifier and mechanical cable connection system. In the clinical sessions, the patient was able to modulate neuron activity and specifically, on multiple occasions, neuronal activity was increased when the patient was instructed to imagine moving his left hand and/or arm. As a control, the patient was asked to imagine leg movement (the array is implanted in the arm area of motor cortex and thus should record no activity if the patient imagines movement of other body parts). As predicted, imagined leg movement did not cause an increase in activity. Preliminary analyses also suggest that some neurons are tuned to movements in certain directions (so-called directional tuning). Another embodiment of the present invention allows an operator, through bi-directional communication, to turn off select channels that do not participate in the movement analysis. It keeps the temperature of the device lower and it reduces the amount of data needed to be transferred, subsequently lowering bandwidth requirements. In such low bandwidth requirements, the IR communication of the present invention may not be required, and an additional communication element such as RF would allow remote placement of the external device receiving communications, such as the controlled device.

The current microelectrode array is a 100 electrode, 10×10 pattern with one millimeter long electrodes configured on a 0.4 mm center-to-center pitch. Experience from the human clinical trial indicates that a wider range of electrode length and pitch coupled with a variable electrode length profile across the array would be highly desirable in order to optimize the probability that a significant number of electrodes may be placed in the correct layer of the motor cortex. The result may be a larger quantity and higher quality of neural units detected and thus better patient control of the neural prosthesis. A preferred embodiment of the present invention includes a sensor with multiple penetrating projections, one or more projections including one or more electrodes. In addition to these signal capturing electrodes, the sensor body includes one or more integral reference surface electrodes, obviating the need for the reference wires, currently placed on the surface of the brain in the surgical procedure. This reference electrode integration may minimize surgical time and risk of damage to the arachnoid membranes overlaying the cortex. Additionally, construction of an outer flange extending radially outward from the projections makes possible the attachment of a removable housing to provide protection to the delicate projections and electrodes during the surgical procedure leading to cortical insertion.

Figure 9:
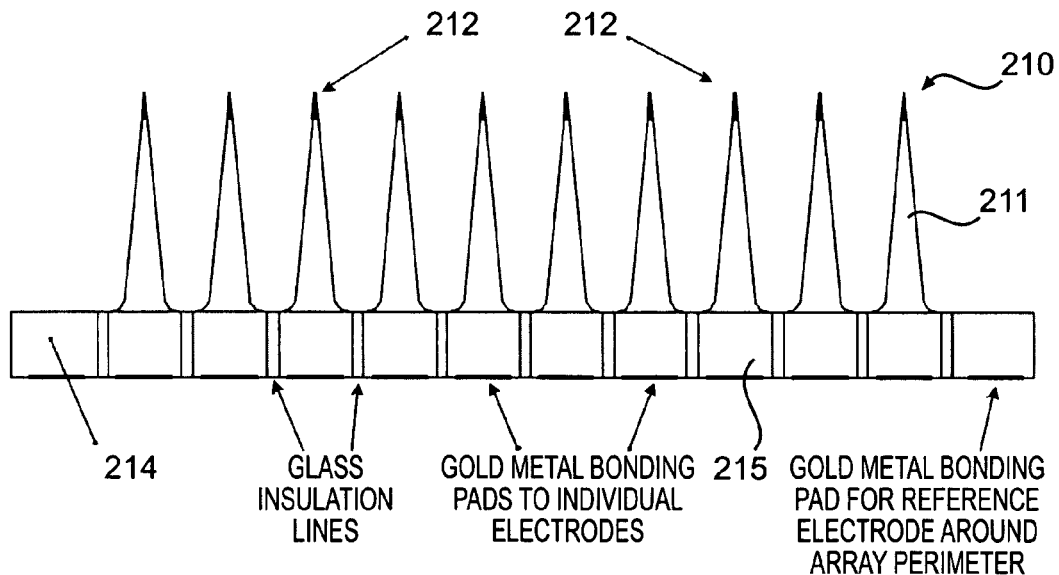
FIG. 9 illustrates a cross-sectional view of the sensor consistent with the present invention.

FIG. 9 illustrates a schematic cross-section of an array design, sensor 200 that incorporates a perimeter flange, flange 214, that can serve as both a surface for one or more reference electrodes, such as flat electrodes that do not penetrate tissue, as well as a structure for anchoring or otherwise securing the sensor 200 to a protective cap or covering, not shown. Sensor 200 includes base 215, preferably a silicon substrate, with multiple projections 211 that have one or more electrodes such as electrode 212 at each tip. Electrode arrays with flanges, and projections 211 of different lengths can be manufactured with a silicon dicing saw with sub-micron precision. This process allows processing of about one hundred arrays per wafer simultaneously. Precision silicon dicing saws combined with appropriate blade dimensions, blade composition and saw control parameters, can produce a wide variety of array architectures. The result of this manufacturing method may be a wider range of array configurations as well as the elimination of numerous processing steps that have the potential to damage the delicate array electrodes. For instance, manufacturing a slant type array can be accomplished by programming the dicing saw to progressively dice individual rows of electrodes such that the height of each electrode row is progressively lower than the proceeding row. It should also be possible to use this precision saw to cut the actual projection profile rather than simply cutting square columns which are then extensively acid etched to create the final shape.

The manufacturing method further includes use of the focused, and programmable beam of the excimer laser to precisely mill off the previously deposited insulating Parylene C polymer from the projection tips to expose the electrode metal beneath. This laser process may yield much greater precision and control of electrode tip exposure. The laser milling capability may be particularly important for slant electrode arrays which may require the insulation removal process.

A method of manufacturing arrays with a perimeter flange 214 structure for handling the array or placing it into a protective holder or protective cap during the surgical tunneling can be done by machining away (via dicing saw) the outside rows of the sensor 200 as depicted in FIG. 9. Such a perimeter flange can also serve as a platform for placing reference electrodes directly onto the back of the array by sputter coating traces onto the back of flange 214. Such a perimeter shelf and the integrated reference electrodes provide a substantial improvement in capability over the current array architecture.

Figure 10:
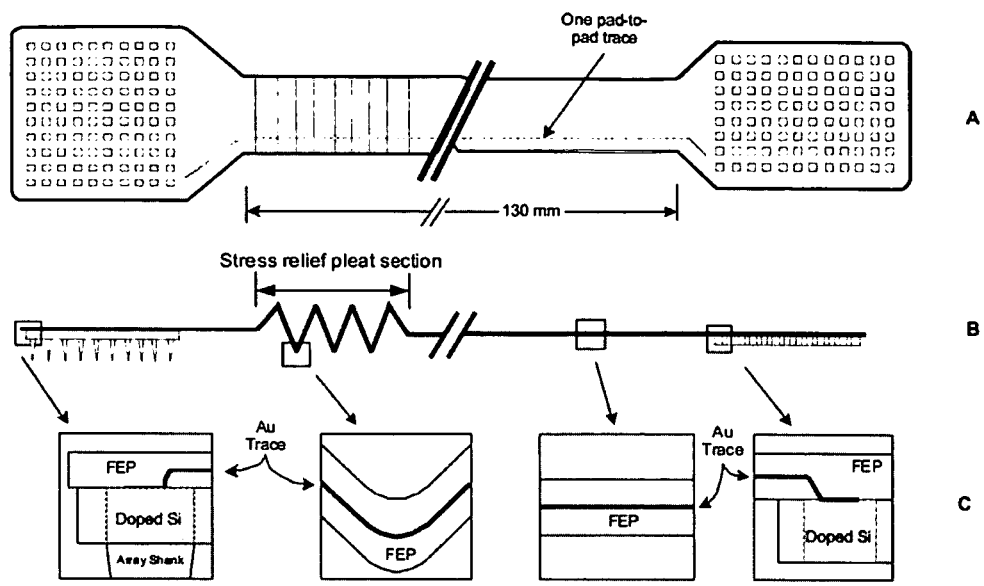
FIG. 10 illustrates multiple views of a ribbon cable consistent with the present invention.

Referring now to FIG. 10, a planar electrical conduit of the present invention is illustrated. In an exemplary embodiment, the planar electrical conduit is a multi-conductor ribbon cable 225. The figure depicts the following: (A) top view of the bonding pad (e.g., conductive pads 226) for the array and the connector ends (actual gold traces 229 and bonding pads would be encased in the FEP membrane and would not be visible from outside); (B) side view showing an expandable portion comprising a set of pleated folds; and (C) sectional views in four key regions of the cable. Also depicted is base 215 of the sensor, with projections 211 and electrodes 212 at the tips. Results of the human clinical trial to date indicate that the implant microwire cable is very difficult to manipulate and route during the implantation process. This difficulty adds considerably to surgical time and poses a risk that the delicate array and cable may be damaged prior to insertion. Furthermore, it is well appreciated that the human brain can move within the skull several millimeters in any direction. Such movement may exert a force on the array via the fixed wire bundle that could dislodge the array from the cortex. The cable design may comprise 96 one mil diameter Au/1% Pd micro-wires each insulated with a thin (~5 µm) polyester layer. The cable wires are consolidated together and overcoated with a layer of medical grade silicone rubber for enhanced bio-stability and mechanical protection. The elastomeric nature of the silicone predominates over the plastic properties of the wires making the cable extremely elastic and springy.

An embodiment of the present invention includes an extremely flexible, non-elastic cable that is integrally incorporated into the implant assembly, simultaneously linking the electrode array to the subcutaneous electronics package. By way of example, the cable is a 100 channel, FEP Teflon based, planar cable of 13 cm long, less than 5 mm wide, and less than 0.05 mm thick. One end of the cable is built directly onto the microelectrode array while the other end is constructed onto the male end of a connector. The non-elastic FEP cable may also have a stress relief feature to provide for easily surgical placement and enhanced in vivo stress relief. Such a planar cable design makes possible the incorporation of such a connector. The stress relief may be able to accommodate brain movements of 3 mm in up to 3 orthogonal directions. The manufacturing process may require photolithography masks that may define the bonding pad geometries on both ends of the cable as well as the trace routing and trace width, length and spacing. A resist spinner-compatible base plate that may serve to precisely hold both the array and male end of the connector plate and may also serve as the base for the planar cable formation during fabrication may be used.

An embodiment of the stepwise construction sequence may begin with placement of both the array and the silicon cable connector pad into recessed cavities in the base plate such that their surfaces are flush with the base plate. The connector pad is similar to the array base in structure and composition. For example, there is a regular pattern of conductive vias (doped silicon) immersed in, but electrically isolated from, the surrounding silicon by nonconductive glass. The plate is approximately 1.2 mm thick. Next, a shield mask is applied over the top of the plate surface. Two apertures in the mask allow the array and the connector bonding pad sides to be exposed to a plasma surface conditioning process that serves to enhance the adhesion of FEP fluorocarbon membrane to the array and connector. Immediately following this, a thin (10-25 µm) FEP membrane would be heat and pressure sealed to the array, connector and base plate. Next, an excimer laser is used to precisely and completely mill away the sections of the fluorocarbon membrane overlaying the bonding pads on both the array and the connector. Next, standard photolithography techniques are used to apply and cure photoresist, expose the resist using the chrome mask, sputter coat gold for the traces and bonding pads to the conductive silicon and remove the residual photoresist and gold. Then a second, thin (10-25 µm) FEP membrane is heat and pressure sealed to the top of the assembly to form a multi-conductor planar cable. The excimer laser would be used to cut through the double FEP sheet around the perimeter of the cable and the completed assembly is removed from the base plate. Finally, a thermoformed pleated stress relief pattern is formed near the array end of the cable using a hot corrugated clamping mandrel. The resulting ribbon cable structure is schematically depicted in FIG. 10.

Figure 11:
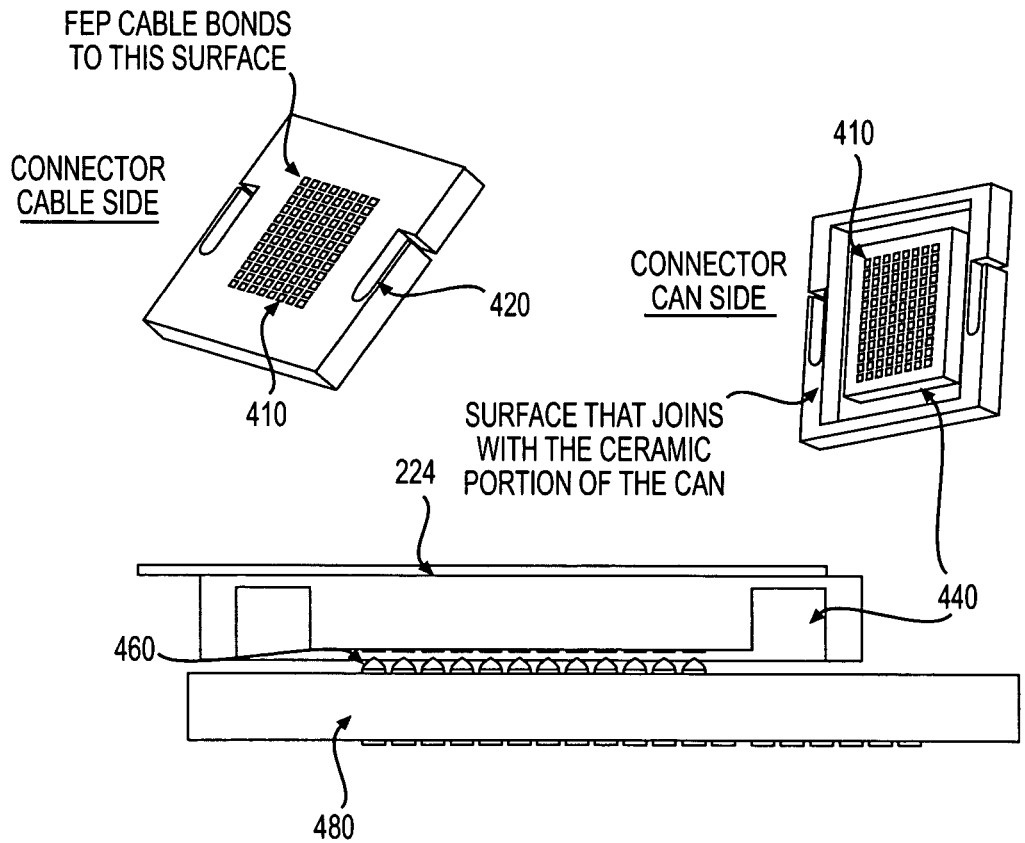
FIG. 11 illustrates multiple views of a large density ribbon cable connector consistent with the present invention.

FIG. 11 depicts a planar cable connector (e.g., detachable connector 230) of the present invention that allows the implanted processing unit portion, when found unfunctional, to be disconnected and replaced while leaving the array of electrodes and planar cable 224, intact in the cortex. The existing implant assembly employs a micro-wire bundle (cable) that is hardwired (via wire bonding technology) to the electrode array and a transcutaneous, through-the-skin connector that is physically attached to the skull. Based upon similar devices, such as cochlear implants, it is likely that a five year failure rate of 5% may be anticipated early in the product development cycle. In this case, any failure in a totally hardwired system would necessitate complete surgical removal via crainiotomy and replacement of the implant, exposing the patient to yet another surgical and a post-surgical infection risk. An embodiment of the present invention minimizes this possibility, by providing a connector system that is integral to the planar cable 224—implanted processing unit package interface. Such a connector may allow the subcutaneous electronics package to be disconnected from the electrode array and replaced for any reason thus eliminating the risk of having to access the brain to remove the array and cable from the cortex should the implanted processing unit "package" fail. This strategy keeps the array and cable relatively simple and reliable and places the more complex (and failure prone) electronics package in an accessible, subcutaneous location beneath the scalp for easy access should intervention be necessary. In an alternative embodiment, the planar cable is attached, without a detachable connector, to the implanted processing unit. In this embodiment, a kit is provided. The kit may include means of cutting or severing the planar cable near the implanted processing unit, a connector which can be attached to the planar cable near the severed end, and a crimping device for providing a seal and making the required electrical connections between the cable and the newly attached connector.

Referring back to FIG. 11, the connector comprises two mating parts, one integrated into the planar cable and the other integrated into the electronics package. During the planar cable construction, the silicon plate connector element is integrally incorporated into the cable. This is possible because the connector plate is very similar in design, composition, and manufacturing approach to that of the array. For example, both may have bonding pad patterns of doped, conductive silicon vias separated by insulating glass lines. The silicon connector plate, approximately 9 mm×9 mm×1.2 mm thick, is manufactured with: 0.250 mm square pads 410 in a pattern of 8×12 with corresponding pitches of 0.4 mm×0.5 mm respectively to match the bonding pad pattern on the Amplifier ASIC in the electronics package; a silicon spring feature 420 constructed into the sides of the connector that may aid in alignment, mating, and fixation of the connector plate with the corresponding pad on the electronics package; and a groove 440 around the bonding pad pattern on the electronics package that may contain a desiccant material serving as a water vapor barrier (getter) to extend the lifetime and hermeticity of the connector. This silicon plate with the integral planar cable mates directly onto a High Temperature Co-fired Ceramic (HTCC) board 480 used to create the feedthroughs to the ASIC inside the electronics can. The HTCC board may have gold stud bumps 460 attached to each pad. When the planar cable connector is snapped into place, these gold stud bumps 460 create contact points that are crushed by the pads on the ribbon cable connector creating the contact force necessary to achieve a good electrical connection. The crushing of the stud bumps accommodates the height variability of the bumps (~10 µm) ensuring good electrical contact for all connections. The result is a silicon connector plate that is flush with the HTCC board. In order to seal the connector, a quick-curing, biocompatible polymer may be applied around the perimeter of the silicone plate. A water vapor getter desiccant material would absorb water that diffuses into and through the silicone barrier over time. Modeling calculations indicate that a getter volume of approximately 15 mm$^3$ (1×1×15 mm perimeter length) of anhydrous calcium sulfate would have sufficient water absorption capacity to maintain connector hermeticity in excess of five years. The planar FEP cable is formed directly and simultaneously onto both the array and the silicon connector plate. The final step in assembly is the connector mating to the electronics package. FIG. 11 illustrates the concept of the connector.

Figure 12:
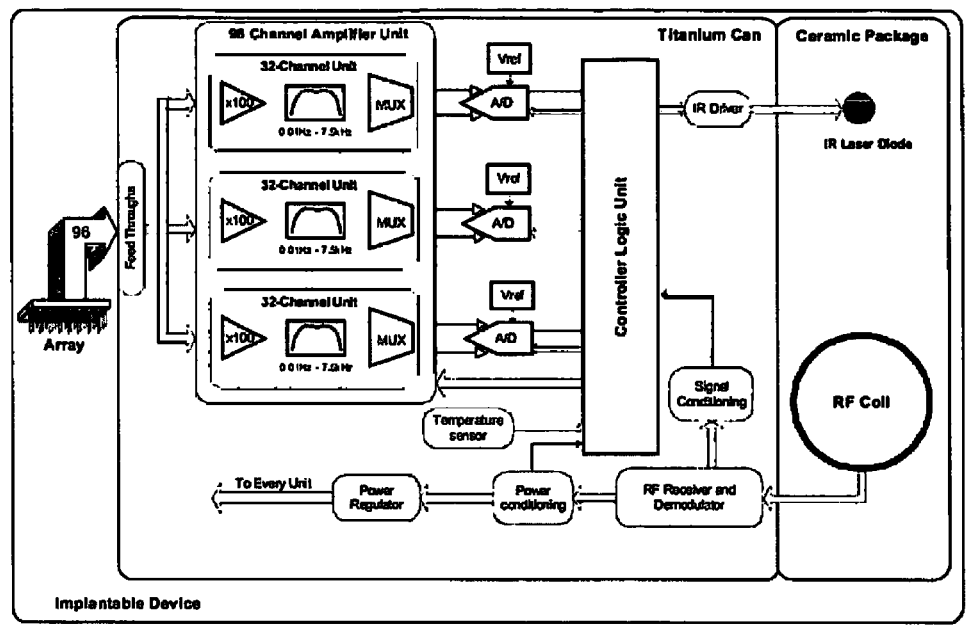
FIG. 12 illustrates a schematic block diagram of an implanted portion of the processing unit consistent with the present invention.

FIG. 12 depicts a functional diagram of the implanted portion of the processing unit, processing unit first portion 130a, of the present invention. Avoiding a through-the-skin device in any system generally leads to improvements in acceptance, safety, reliability and performance. An embodiment of the present invention is an implanted portion of the processing unit, processing unit first portion 130a, which communicates with external devices with wireless communication. Another embodiment of the present invention provides safety features that mitigate temperature and power fluctuations and protect from electrostatic discharge (ESD). A method to measure in vivo impedance at the time of implantation is also described which may help determine if the array was inserted properly and may function as desired, as well as diagnose adverse changes to one or more of the implants. One embodiment of the present invention provides an implantable VLSI amplifier and controller unit with the power and telemetry for high speed data collection and transmission.

A functional diagram of the implantable processing unit depicted in FIG. 12 illustrates two Application Specific Integrated Circuits (ASIC) made up of the Neural Signal Amplifier with Analog Multiplexers and the Controller Logic Unit. The ASIC and other functional electronics are housed in a hermetic titanium can incorporating 100 feed-throughs. The data and power transmission portion of the system are housed in an adjacent ceramic package. The implantable processing unit includes wireless, through-skin telemetry with high speed data transmission, an inductively coupled power source, two-way communication system diagnostics, and enhanced safety. A 96-channel amplifier with ESD protection is described which may not allow significant DC current to pass from the implant back to the implanted electrodes in case of an ESD event. The implantable processing unit includes: a Data Acquisition Mode which produces a serial data stream containing neural signal recordings and safety-related information and a Test Mode which provides information about the condition of the implant; and two-way telemetry communication with high speed IR data out and RF power and control signal in. In an alternative embodiment, an implanted power supply such as a rechargeable battery and/or an RF transmitter are also included. Typically, all communications may be checked using data integrity measures including 8b/10b encoding and checksum. The integral impedance test may have a maximum of 10 nA current injection to avoid cortical stimulation.

The electronic module includes two primary VLSI electronic components. The first is a 96-channel amplifier with special ESD protection. All VLSI circuits include some protection from damage by electrostatic discharges into device pads and connection points, but they are not optimized for microelectrode inputs, and they often have single diodes between the electrode input and power source. In a single fault failure case, this can apply power to the electrode input and damage the neural tissue.

Access to each individual channel is necessary for channel selection and impedance checking. Channel selection can reduce the number of channels being recorded which would in turn reduce both the required outgoing data rate and overall power dissipation of the system. Accessing individual channels is essential to closing the loop needed for measuring electrode impedance. The reference electrode switches to the current limiter output of a 1 kHz generator, and the reference input of the differential input amplifier of the individual channel switches to ground.

The sampling speed of each channel is set at 30 ksps to match that of the Braingate System currently in clinical trials. Given the 30 ksps sampling rate per channel, a 3 Msps ADC would be required. However, the maximum speed of the appropriate ADC may be 1-1.5 Msps. Separating the 96-channels into three 32-channel banks may allow the system to use low power A/D converters. Three A/D converters may be used to obtain the desired sampling rate while maintaining low power dissipation.

Figure 13:
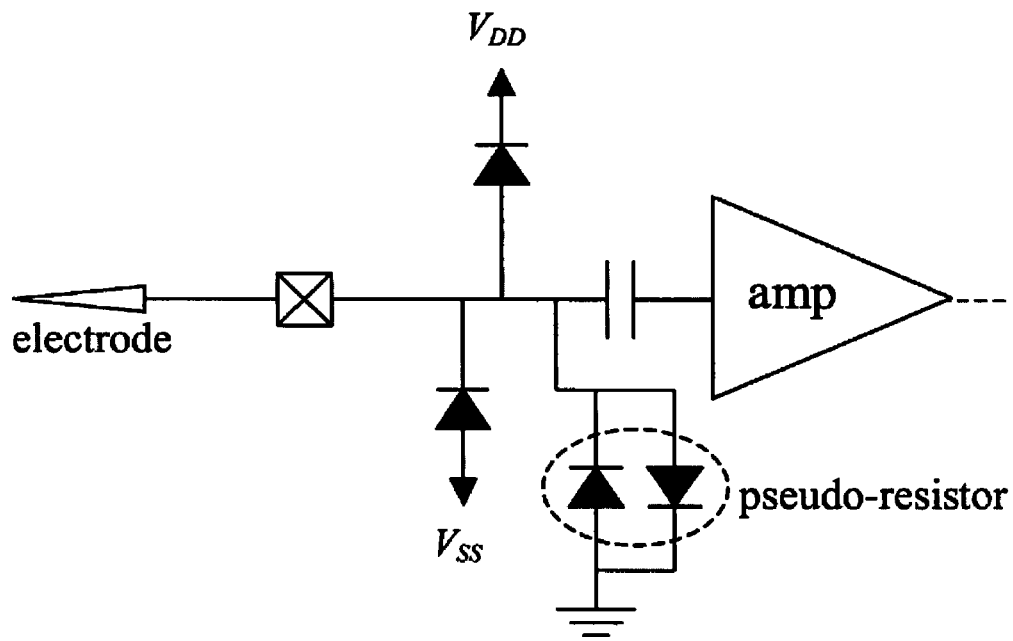
FIG. 13 illustrates a schematic of an ESD protection circuit consistent with the present invention.

Referring now to FIG. 13, a schematic of an ESD protection circuit of the present invention with a pseudo-resistor to limit electrode voltage in a fault situation is shown. This ESD protection circuit guards the sensitive integrated CMOS amplifier inputs from electrostatic damage during or after implantation. Of particular concern is the fault tolerance of ESD protection schemes and their failure modes. The ESD protection circuitry should protect the AC coupling capacitor sufficiently such that an ESD event cannot break down the capacitor oxide and cause DC current to pass through the capacitor. An ESD event should not cause damage to the ESD protection circuitry in any way that would allow DC current to flow through the protection circuitry and into the electrode.

Figure 14:
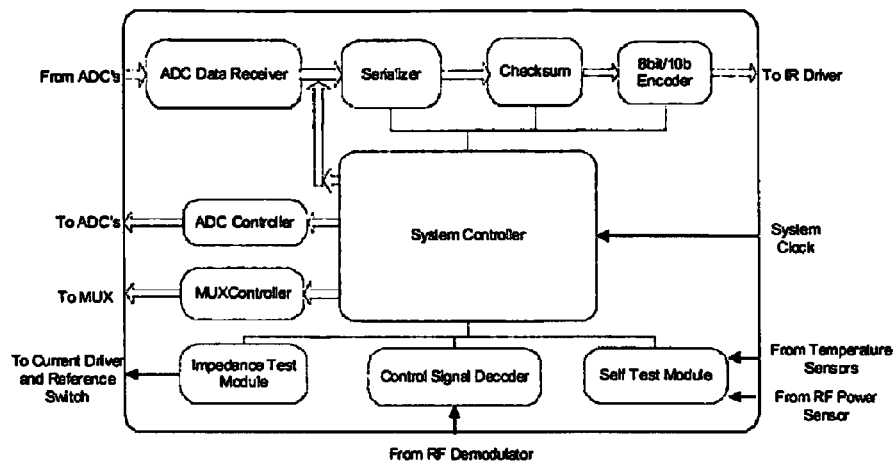
FIG. 14 illustrates a functional diagram of the Control Logic Unit of the implanted portion of the processing unit consistent with the present invention.

Referring now to FIG. 14, a functional diagram of the Control Logic Unit is depicted. The second VLSI design is a Controller Logic Unit, which supervises the neural data acquisition and the functional and safety testing units. To communicate with the implanted device, a hybrid two-way telemetry is utilized. Neural and test information coming from the Control Logic Unit may be transferred via IR optical transmission. This is a high-speed (50 Mbs) data link. To control the different functions of the Controller Logic Unit, a significantly lower data transfer may be appropriate (in kHz range). Inductively coupled RF power link carries this low data transfer information by modulating its carrier frequency. After demodulating the information, the Control Signal Decoder Unit may conduct a data validation to prevent false or corrupted data from being read by the implant.

Figure 15:
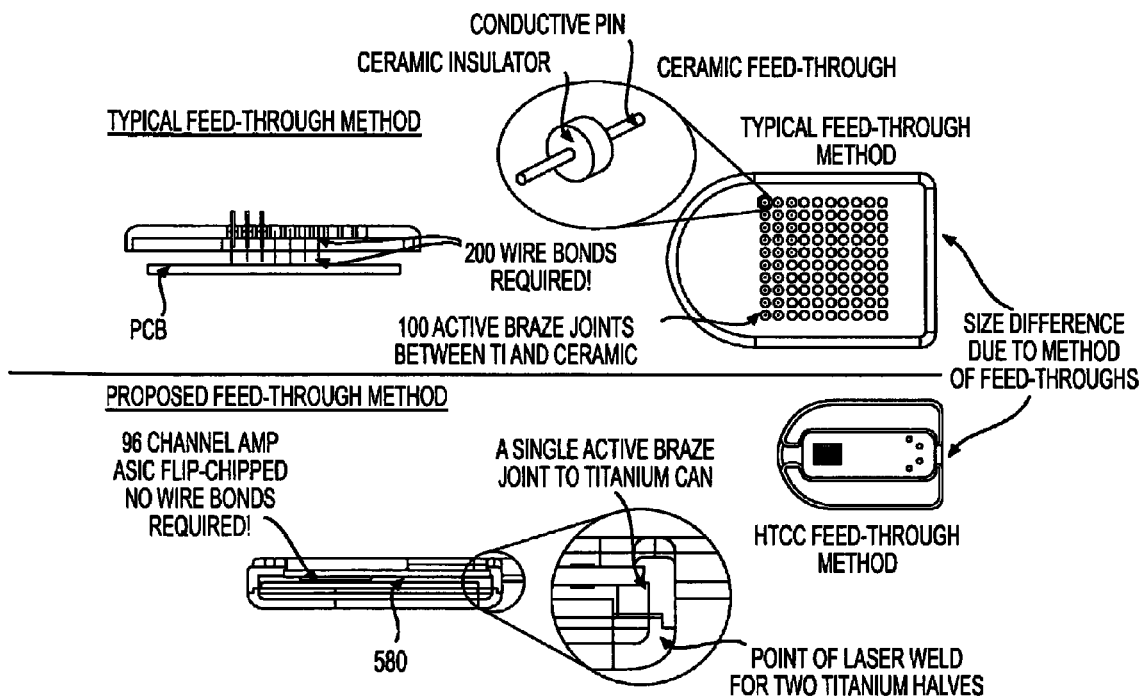
FIG. 15 illustrates two feed-through designs for connecting a large number of conductors cable to a hermetically sealed implanted portion of the processing unit consistent with the present invention.

Referring now to FIG. 15, two feed-through designs are depicted for connecting a large number of conductor cable to a hermetically sealed device. An embodiment of the present invention may include a design and method for creating electrical hermetic feed-throughs, which reduces the pitch between the feed-throughs, uses a single joining step for all of them rather than one for each, makes it possible to attach electronic components directly onto the feed-throughs, and can be used in implanted medical device applications. A can assembly is composed of two laser welded titanium shells with a High Temperature Co-Fired Ceramic (HTCC) window, with 100 filled, through hole vias, brazed onto the can and hermetically tested to a level of 10-8 cm3/sec of He. The ASIC is flip-chipped to the HTCC board, hermetically sealed inside the can and verified for electrical contact between the outside of the can and the ASIC.

The typical method for doing a hermetic feed-through involves individual wires with either ceramic or glass cylinders hermetically sealed to them, as shown in the upper portion of FIG. 15. These glass or ceramic cylinders are then melted or brazed to the can wall. The minimum pitch between feed-throughs of this type is ≈2.5 mm (0.100 in). With over 100 separate braze joints, the likelihood that at least one may fail hermetically is high. There are also 100 more wire connections to be made in this case since the feed-through needs to be connected to the electronics within the can. These issues are illustrated in FIG. 15. For reasons of size and reliability the traditional method of creating hermetic feed-throughs is not practical.

As shown in the lower portion of FIG. 15, an embodiment of an implatable processing unit portion of the present invention may include HTCC (High Temperature Co-fired Ceramic) board 580 comprising alumina substrate and tungsten traces (both known for their biocompatibility and biostability) used to create the 100 feed-throughs. The HTCC boards 580 are processed by sputter coating a titanium/tungsten (Ti/W) layer onto the pads followed by platinum (Pt) providing a biocompatible surface acceptable for wire bonding. This process may create a board with filled, through hole, vias in a pattern matching that of the pads on our amplifier ASIC which is responsible for receiving the signals from the sensor.

Figure 16:
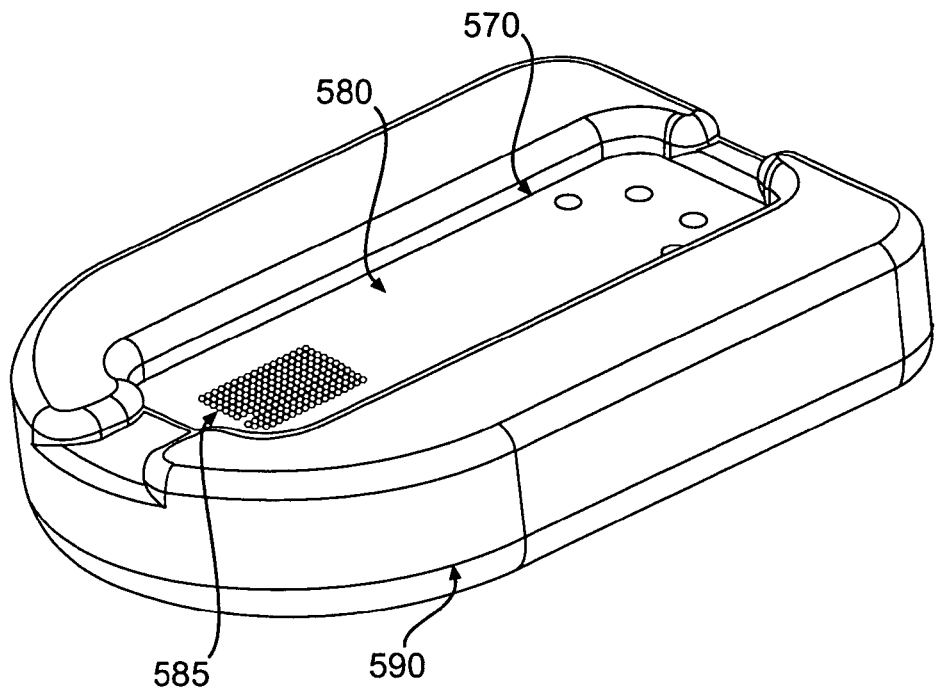
FIG. 16 illustrates a feed-through design for connecting a large number of conductors cable to a hermetically sealed implanted portion of the processing unit consistent with the present invention.

FIG. 16 illustrates an exemplary embodiment of the feed-through for processing unit first portion 130a. By brazing the HTCC board 580 into a window in one half of a titanium can at active braze seam 570, this single brazed component provides 106 filled vias (instead of feed-throughs). The ASIC may be flip-chipped directly onto these vias on the inside of the can, eliminating the complex and risky step of wiring from the can to the internal electronics. From this point, the rest of the electrical components are placed inside the can and the cover laser welded at laser weld seam 590, creating a hermetic seal meeting the requirement of 10-8 cm3/sec of He. The amplifier electronics are powered through RF coupling with an RF coil hermetically sealed within a biocompatible package. The IR laser diode is driven with the amplifier electronics while being powered by RF coupling.

The external processing unit portion may use magnets to align the RF power coil. In addition, the magnets may hold the internal and external optical elements of the high-speed IR data transmission fixed to within ±2 mm of one another under normal use. The power requirements of the implant are 150 mW as compared to 15 mW for a cochlear implant. To supply the additional power, an inductive scheme incorporating approximately 42 windings of 100 strand Litz wire hermetically sealed within the can is used.

Figure 17:
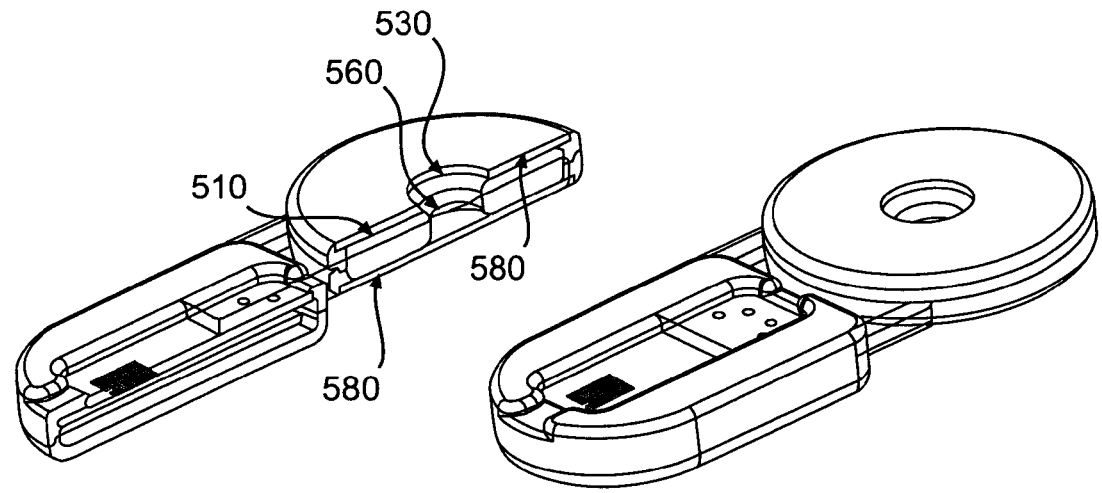
FIG. 17 illustrates an implanted portion of the processing unit consistent with the present invention.

Referring to FIG. 17, a hermetic package of processing unit first portion 130a is depicted, including RF and IR elements. Most of the electronics of the device need to be shielded from EMI in a titanium housing. However, the RF coil 610 may require an unshielded hermetic environment. Two titanium rings each have an HTCC ceramic (e.g., $Al_2O_3$) board actively brazed to it. One of the ceramic plates has a sapphire window 530 brazed into the middle for the IR data link while the other has the circuitry needed for the IR laser diode 560 and RF coil 610. Five filled, through-hole vias act as feed-throughs to pass power and data between the two cans.

Figure 18:
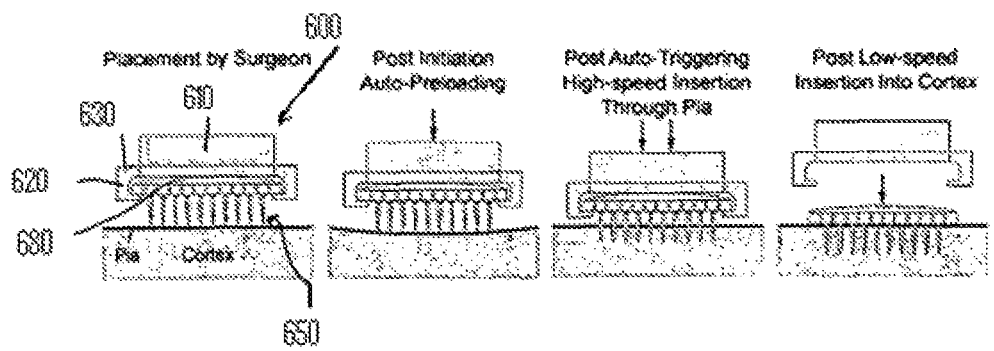
FIG. 18 illustrates an electrode array inserter and a method of insertion of a multiple projection array of electrodes consistent with the present invention.

Referring now to FIG. 18, an electrode array inserter 600, and a method of insertion of a multiple projection array of electrodes is illustrated. The inserter 600 includes a force measuring element, such as a strain gauge or pressure transducer, not shown, to provide an automatic trigger for activation of an inserter piston 610 at the appropriate tissue preload.

The inserter 600 has a casing 620 having first and second ends and enclosing a chamber. A piston 610 disposed within the casing 620 and slidable between a first and a second position. Piston actuator, not shown, but one or many types of linear actuators, are operably associated with said piston 610 for urging said piston to the second position. The piston includes piston attachment means, such as a mechanical connector, magnetic connector, Velcro, frictional engagement surface, or other connector for attaching the piston to the electrode array or protective cap. The inserter 600 includes array holder 630 for holding the array 650 or the array protective cap 680, such as via frictional engagement with a flange on the array, such that the piston mechanism can not only cause the array to accelerate but also decelerate. In an exemplary embodiment, a protective cap or covering is frictionally engaged with opposing side of the base of the array, in the flange area, and the inserter mates with the protective cap. The holding of the array also prevents a momentum based overshoot which cause the local tissue to deform and potentially become traumatized. Studies of insertions into cortical tissue have shown that success is dependant on a combination of insertion parameters and tissue preload. For example, one has to push the array down onto the cortex until the pial membrane is under tension.

Over-insertion which can result in sub- and epidural hemorrhage, spreading depression, and more permanent brain damage. Cat and monkey cortical implantations have shown that the effects of spreading depression, resulting in a failure to record single unit activity, can range from a few minutes up to 24 hours in duration. The cause of tissue damage is the fact that the array's momentum used to penetrate the outer membranes, mostly the pia, is transferred into the tissue causing temporary dimpling even during a successful implantation.

The most challenging part of array insertion is the penetration of the pia; the underlying cortical tissue does not provide much resistance to the electrodes. Inserters with two speeds, accomplished by electronic or mechanical means incorporated into the inserter, can accomplish complete insertion while avoiding tissue trauma by reducing tissue displacement and preventing over-insertion. To reduce momentum transfer into the tissue and, hence, reduce damage, the array may be held securely at the inserter tip. This may give the ability for a high speed insertion to overcome the pia and slow down the insertion afterwards to keep the brain from absorbing this momentum. It may also allow controlled insertion of varying length and shape electrode arrays. The inserter wand may be attachable to a stereotactic frame and able to be positioned using micromanipulators. The inserter can employ a combination of cams and springs, or an electrical linear actuator, such as a high speed stepper motor, or multiple coil solenoid, to function as an adjustable speed and stroke distance device. This inserter can perform non-continuous motions such as those employing an initial high rate acceleration followed by a deceleration. Other non-continuous motions can include other changes in velocity, direction, acceleration, and momentum, as well as including stepped advances including multiple discrete steps. In another exemplary embodiment, multiple heated Nitinol wires, attached to levers to increase stroke distance and/or provide a mechanical advantage, or selectively actuated by integral electronics and battery of the inserter combined with a user interface to adjust insertion parameters.

Another embodiment of the present invention, a single mechanical protecting cover or cap is disclosed. The protecting cover frictionally engages the array along a flange, and protects the delicate projections of the array during manufacturing, sterilization, shipment, unpacking and tunneling under the skin. As mentioned hereabove, a rim having the width of an extra row of projections is added to the base of the electrode array on each side and used to hold the array in the protective array cover and during array insertion. The mechanism of choice fulfills two criteria: (i) positioning of the array in and removal from the holder in a straightforward and safe manner; and (ii) preventing the array from significantly moving laterally or vertically while held during high speed insertion. This array holder is attached/detached easily to/from the inserter wand.

Studies have shown that, using the pneumatically actuated inserter, complete array insertion can be achieved with an insertion speed above 8.3 m/s but while increasing insertion speed much beyond that point still resulted in complete implantation, it also increased tissue trauma. Because momentum transfer to the tissue may be greatly reduced with the present embodiment, increasing insertion speeds may not affect the brain's response and may aid in the insertion process by making use of the viscous and inertial properties of the tissue. In an exemplary embodiment, the inserter is configured to travel at a speed above 10 m/s for 50-75% of the insertion depth depending on electrode length and array base thickness; after which a much lower speed may be utilized to push the array in the rest of the way. Because the array is always oriented correctly to the cortical surface, reliable insertion of non-uniform or slanted electrode arrays is possible if the device is able to maintain a constant insertion speed until the last electrode tip penetrates the pia.

The tissue preload is an important factor because stretching the pial surface makes penetration easier. The preloading mechanism can be automated. The surgeon should place the array on the cortex with less than 0.5 mm accuracy. Once insertion is triggered, the inserter wand may move towards the cortex at a low speed. As the array pushes down on the cortex, the load on the inserter tip may increase. High speed insertion is triggered at a predetermined applied load via a load measuring element integral to the inserter which is tied to the trigger. Because breathing can change this force over time, this mechanism may eliminate the need to time the insertion with the breathing artifact and only trigger when the applied load is sufficient. This load may be determined based on the insertion speed of the inserter. Once partial insertion is achieved using high speed insertion, the low speed advancement, still in progress, may complete implantation. Hence, the mechanism to apply preload may also be used to slowly advance the array to achieve complete insertion.

Figure 19:
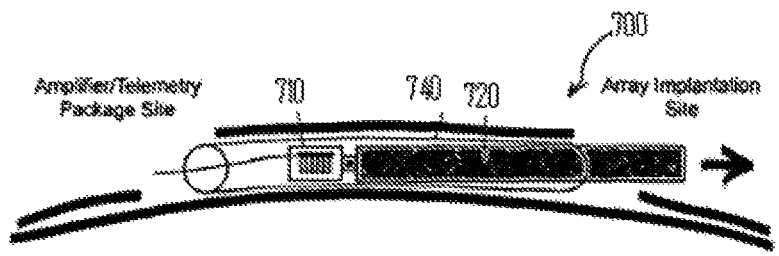
FIG. 19 illustrates a tunneling tool and a method of tunneling with the array attached to the shaft consistent with the present invention.

Referring now to FIG. 19, a method of tunneling with the sensor 200, an electrode array, attached to the shaft of a tunneling device (e.g., tunneler 700) is illustrated. The tunneler shaft 720 can be attached to the array 200 at the base, wire bundle, and/or protective cap of the array 200. The tunneling shaft 720 may have a detachable tip. The attachment member can includes magnets, hooks, frictional engagement means, Velcro, and the like. In an exemplary embodiment of the present invention, surgical templates, not shown, and other tools are provided to aid in the selection of the proper location for one or more implants, as well as to aid in the modification or forming of one or more wire bundles or ribbon cables. The wire bundle of the present invention is sized to reach any area of the cortex that is on the same side as the implanted portion of the processing unit. A system which utilizes one wire bundle length to accomplish this simplifies purchase for implanting hospitals. A single, long wire bundle may require manipulation to fit into cortex that is at different distances from the implanted processing unit "can". In an exemplary embodiment, a template and a wire winding tool are provided, in combination telling the surgeon exactly how to form the wire bundle to fit between the array implant site and the "can" implant site. The winding tool can be used to create one or more bends in the wire bundle, the tool including one or more cylindrical projections containing specific diameters for the winding process. Winding of a portion of the wire bundle around the specific diameter may cause the wire to assume a pre-determined shape.

From the implant location of the "can," e.g., behind the ear, the surgeon may use a template from the "can" to the position where the array would pass through a craniotomy and to the brain. The template includes instructions imprinted on its surface describing how to bend, twist, wind, or otherwise shape the wire bundle for a desired fit in the desired location. Along with the template, a winding or shaping tool is provided that the surgeon uses on the wire bundle, following template instructions, e.g., "wind wire-bundle middle around supplied mandrill B three times". The template design might be adjustable. At each adjustment setting, the proper instructions are shown. Surgical templates may also aid in the selection of the proper location and in the creation of the bone well for the implanted signal processing portion including amplifier and telemetry unit.

Also described are tunneling tools and a surgical procedure that allows safe tunneling of the electrode array from the placement site of the amplifier and telemetry package to the array implantation site. An array cover 710 protects the array 200 from damage, debris, blood, and other fluids during handling in the operating room, tunneling under the skin, wire bundle manipulation before array insertion and possibly during insertion.

Templates can be used for one or more of the following functions: determine amplifier/telemetry package location; determine skull groove location and shape for the wire bundle; trace the opening and aid in creation of recess using a drill; check the created recess; and combinations thereof. A template may be added to help during the craniotomy procedure. The materials of choice for these templates are stainless steel or titanium.

The most delicate features on an electrode implant are the 100 projections containing the electrodes. They are preferably made out of silicon, are only a few micrometers wide at the tip, and, hence, break easily on contact. In addition, insertion of and tissue reaction to the implant are negatively affected by blood and other debris on the electrodes. To minimize these risks, the array cover 710 is provided to protect the array during surgery. Additional gripping of the wire bundle close to the array by the protective cover 710 may decrease the likelihood of damage even further by, for example, providing some resistance to axial pulling.

As mentioned hereabove, tunneling of the electrode array from the amplifier/telemetry package may be necessary to minimize the surgical risks associated with large incisions and to allow array implantation in any cortical area ipsilateral to the implanted processing unit portion. The tunneling tools allow safe tunneling of the array under the skin from the amplifier/telemetry package to the array implantation site. The tunneling tool set comprises the following components: a shaft 720, such as a deformable metal shaft, used during the creation of the tunnel and possibly also used to pull the array in the cover through; a sleeve 740 to fit around the shaft, such as a wire enforced elastomeric sleeve or a peel away sleeve, that may serve as a 'tunnel' when the array and cover are pulled through; a detachable shaft tip that may aid in creating the tunnel and protect the sleeve from contamination. In an exemplary embodiment, the tunneling tool includes a detachable tip for the shaft that may allow simplified attachment of the array in the cover.

The tunneling tools are manufactured in an assembled state: sleeve 740 on shaft 720 and tunneling tip(s) attached. The maximum outer diameter of the tool may typically be 12 mm. The tunneling shaft 720 can be constructed of various materials such as stainless steel or titanium, and of various shapes to conform to different skull sizes and shapes. The surgeon may be able further bend the shaft for more precise tunneling. The sleeve, or sheath, sheath 740, is made of PTFE or some other flexible material. The maximum length of the sheath 740 may typically be 20 cm allowing tunneling to any ipsilateral cortical area. In an exemplary embodiment, sleeve 740 is wire reinforced to maintain a minimum inside diameter along its length. In another exemplary embodiment, sleeve 740 is scored along its length to allow sleeve 740 to be peeled into a pair of sheath portions. In another exemplary embodiment, sleeve 740 remains implanted in the patient.

As described earlier, several mechanisms can be provided to attach the array cover either to the shaft 720, a separate tip on the shaft, or the sleeve 740 of the tunneling tool (see FIG. 19). These mechanisms may include the use of magnets, a hook/ring combination, or key-like features on both the tunneling tool and the array protective cover. Because of limited axial strength of the wire bundle and the bonds on the back of the array, the array cover 710 should be prevented from getting stuck on its way through the tunnel. The magnet embodiment provides a means to release the cover when tension increases. Another embodiment is to remove the shaft 720 from the tunnel and attach the cover to the sleeve; after which both are pulled through at the same time.

Figure 20:
FIG. 20 illustrates a schematic of a switching circuit for an impedance analysis device consistent with the present invention.

Referring now to FIG. 20, a schematic of an exemplary circuit for an integral impedance measurement device is shown. The ground attached to the package is switchable between closed and open connection state. The system may separately switch every channel on and off. No two channels are activated at the same time. On every channel, the reference input of the differential front amplifier is switched separately. The system may include another set of multiplexers, which can be controlled in parallel with the channel multiplexer. The reference input to ground may switch and the reference electrode may be floating.

To the floating reference electrode input, a frequency generator is connected through a current limiting resistor. In an exemplary embodiment, the current is limited to a maximum of 10 nA to prevent any damage to stimulation of patient cells. The frequency generator is preferable operating on two separate frequencies such as 1 kHz and 500 Hz, enabling the measurement at two points of the impedance function to diagnose what might be causing a rise or fall in impedance. The signal generated can be a sine wave or square wave, and can be divided from a clock signal.

The diagram of FIG. 20 shows how the configuration of the switches when set to impedance testing (except the GND-Case disconnection). The measuring loop is the generator (with one output compared to GND), the resistor (the resistance the Frequency Generator and Reference electrode), the reference electrode, input from selected channel, and the input of the differential amplifier. The amplifier works such that, if one input is grounded, the other may be on "virtual ground" (high impedance current drain with very low leakage). This connection closes the loop. The amplifier's output voltage may be proportional to the current flowing into this "virtual ground".

The output voltage is proportional to the input current of the amplifier:

$$V_{out}=A*I,$$

where:
$V_{out}$ is the output voltage,
A is the amplification factor, and
I is the input current.
In the measurement loop, the current may be:

$$I=V_{gen}/(R_{limiter}+Z_{ref}+Z_{electrode}+Z_{input}),$$

where:
I is the input current to amplifier,
$V_{gen}$ is the output voltage of frequency generator,
$R_{limiter}$ limits the maximum current,
$Z_{ref}$ is the impedance of reference electrode (which is very low compared to electrodes),
$Z_{electrode}$ is the electrode impedance,
$Z_{input}$ is the additional impedance at the input of amplifier (similar to capacitive coupling),
In the model, if the resistances are set to zero, the current may be:

$$I=V_{gen}/R_{limiter}.$$

This current is set to approximately 10 nA or less to stay below currents usually used in stimulation procedures, such as neural stimulation procedures.

From the equations:

$$Z_{electrode}=(V_{gen}*A/V_{out})-(R_{limiter}+Z_{input}+Z_{ref})$$

In order to perform the impedance measurement, the following steps are taken: (i) set the channel which you want to measure in the manner described above; (ii) switch the case GND to a floating condition (disconnected); (iii) set the frequency generator to 1 kHZ; (iv) measure the square wave amplitude; (v) calculate the impedance using the amplitude of frequency generator signal and the amplitude of the measured signal. This test may be performed from a direct command sent to the Control Logic of the implant, either from the implant itself, or an outside communicating device.

In an exemplary embodiment, the impedance information is used to modify one or more parameters or otherwise alter the signal processing, such as to change the channels being processed or a specific coefficient or other parameter of that channel, such as a channel whose impedance has increased. Such automatic, semi-automatic, or manual parameter change is consistent with the adaptive processing embodiments of the present application. In the case of an open connection, such as a broken wire or broken projection containing an electrode, the impedance test can be used to differentiate an electrode not receiving cellular activity versus a broken connection to that electrode. Electrical shorts or near shorts can be detected with the impedance testing as well, and in combination with other tests that can be performed, can create a sophisticated self diagnostic device. Alternatively or additionally, the impedance test can be commanded from an external device providing two way communication with the implanted portion of the processing unit. The external device can be used to determine the impedance measurements to be taken, and data can be retrieved from these tests or self-tests of the impedances of the system.

Numerous methods are provided in the multiple embodiments of the disclosed invention. A preferred method embodiment includes a method of selecting a specific device to be controlled by the processed signals of a biological interface system. The method comprises the steps of: providing a biological interface system for collecting multicellular signals emanating from one or more living cells of a patient and for transmitting processed signals to control a device. The biological interface system comprises: a sensor for detecting the multicellular signals, the sensor comprising a plurality of electrodes to allow for detection of the multicellular signals; a processing unit for receiving the multicellular signals from the sensor, for processing the multicellular signals to produce processed signals, and for transmitting the processed signals; a first controlled device for receiving the processed signals; a second controlled device for receiving the processed signals; and a selector module that is used to select the specific device to be controlled by the processed signals.

It should be understood that numerous other configurations of the systems, devices, and methods described herein can be employed without departing from the spirit or scope of this application. It should be understood that the system includes multiple functional components, such as a sensor for detecting multicellular signals, a processing unit for processing the multicellular signals to produce processed signals, and the controlled device that is controlled by the processed signals. Different from the logical components are physical or discrete components, which may include a portion of a logical component, an entire logical component and combinations of portions of logical components and entire logical components. These discrete components may communicate or transfer information to or from each other, or communicate with devices outside the system. In each system, physical wires, such as electrical wires or optical fibers, can be used to transfer information between discrete components, or wireless communication means can be utilized. Each physical cable can be permanently attached to a discrete component, or can include attachment means to allow attachment and potentially allow, but not necessarily permit, detachment. Physical cables can be permanently attached at one end, and include attachment means at the other.

The cellular sensors of the systems of this application can take various forms, including multiple discrete component forms, such as multiple penetrating arrays that can be placed at different locations within the body of a patient. The processing unit of the systems of this application can also be contained in a single discrete component or multiple discrete components, such as a system with one portion of the processing unit implanted in the patient, and a separate portion of the processing unit external to the body of the patient. The sensors and other system components may be utilized for short term applications, such as applications less than twenty four hours, sub-chronic applications such as applications less than thirty days, and chronic applications. Additional sensors can be incorporated into one or more discrete components of the system. Sensors can include but are not limited to: a cellular sensor such as a neural sensor, an EKG sensor, a glucose sensor, a respiratory sensor; a blood analysis sensor; an activity or motion sensor; an environmental sensor; a temperature sensor; a strain gauge, a power monitoring sensor; an electromagnetic field sensor; a position sensor; an accelerometer; an audio sensor such as a microphone; a visual sensor such as a photodiode; and combinations thereof. The signals produced by these sensors can be processed by the system to produce the controlled device processed signals and additionally or alternatively be used in one or more system safety, configuration or performance enhancing routines. These second processed signals can be use for one or more of the following: modification of one or more parameters of the system; cease control of the device; reset the system; modify the control of the controlled device; control a second controlled device; and combinations thereof. The sensors external to the patient or implanted, and the signals from the sensors can be transmitted via wired or wireless means. The sensors can be integral to an implant separate from the implants of the present invention. Processing units may include various signal conditioning elements such as amplifiers, filters, signal multiplexing circuitry, signal transformation circuitry and numerous other signal processing elements. In an exemplary embodiment, an integrated spike sorting function is included, such as a minimum amplitude threshold spike sorting function. The processing units performs various signal processing functions including but not limited to: amplification, filtering, sorting, conditioning, translating, interpreting, encoding, decoding, combining, extracting, sampling, multiplexing, analog-to-digital converting, digital to analog converting, mathematically transforming and/or otherwise processing cellular signals to generate a control signal for transmission to a controllable device. Numerous algorithms, mathematical and software techniques can be utilized by the processing unit to create the desired control signal. The processing unit may utilize neural net software routines to map cellular signals into desired device control signals. Individual cellular signals may be assigned to a specific use in the system. The specific use may be determined by having the patient attempt an imagined movement or other imagined state. For most applications, it is preferred that that the cellular signals be under the voluntary control of the patient. The processing unit may mathematically combine various cellular signals to create a processed signal for device control.

Other embodiments of the invention may be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A cellular access system comprising:
    a sensor for placing multiple electrodes in close proximity to living cells below a tissue surface of a patient, the sensor comprising:
    a base having a top surface and a bottom surface;
    a plurality of projections extending from the bottom surface of the base, one or more of the projections including at least one electrode along its length;
    a signal connector linked with the at least one electrode for providing an electrical connection to the electrode; and
    a protective cap configured to protect one or more of the projections;
    wherein a pattern of the projections in the base defines a periphery, and the base comprises a flange portion extending radially outward from at least a portion of the periphery, and
    wherein the protective cap is configured to engage the flange portion,
    further comprising
        a tunneling device for passing the sensor under the skin of the patient,
        a flexible sheath which is placed under the skin after which the sensor is passed therethrough, wherein the flexible sheath comprises a separator for dividing the sheath into a pair of peelable sheath portions.

2. The system of claim 1, wherein the base is constructed of a rigid material.
3. The system of claim 1, wherein the base is constructed of a flexible material.
4. The system of claim 1, wherein the base comprises flexible and rigid portions.
5. The system of claim 1, wherein the top surface of the base comprises a conductive pad for providing an electrical connection to each of the electrodes.
6. The system of claim 1, wherein at least one projection is tapered.
7. The system of claim 1, wherein at least one projection does not comprise an electrode.
8. The system of claim 7, wherein the projection that does not comprise an electrode is configured to anchor the sensor to tissue of the patient.
9. The system of claim 1, wherein at least one of the projections comprises a conductive material and an insulating material.
10. The system of claim 1, wherein one of the projections is separated from another of the projections by an insulating material.
11. The system of claim 1, wherein at least one of the projections comprises an electrode at its distal end.
12. The system of claim 1, wherein at least one of the projections comprises multiple electrodes.
13. The system of claim 12, wherein the at least one of the projections comprises a serial electrical connection with the multiple electrodes.
14. The system of claim 12, wherein each electrode comprises an independent electrical connection.
15. The system of claim 1, wherein the plurality of projections comprises a first projection and a second projection, the first projection having a geometric shape different from a geometric shape of the second projection.
16. The system of claim 1, wherein the plurality of projections comprises a first projection and a second projection, the first projection having a length different from a length of the second projection.
17. The system of claim 1, wherein the electrode is configured to receive one or more cellular signals.
18. The system of claim 1, wherein the electrode is configured to transmit signals.
19. The system of claim 18, wherein the signal transmitted is configured to stimulate one or more living cells of the patient.
20. The system of claim 1, wherein at least one of the projections comprises a conductive pathway along a majority of its length.
21. The system of claim 20, wherein the conductive pathway is surrounded by an insulating material.
22. The system of claim 1, wherein the plurality of projections comprises more than two electrodes, and the signal connector is linked with the electrodes for providing the electrical connection to each of the electrodes individually.
23. The system of claim 1, wherein the protective cap is configured to protect one or more of the projections during: manufacturing; shipment; sterilization; a surgical procedure; a craniotomy; a tunneling procedure of the base and projections under skin; insertion of one or more projections, into tissue; and any combination thereof.
24. The system of claim 1, wherein the protective cap is configured to protect one or more of the projections during a tunneling procedure from a first opening in the scalp of the patient to a second opening in the scalp of the patient.
25. The system of claim 1, wherein the protective cap is configured to protect one or more of the projections during a tunneling procedure from an opening in the scalp of the patient to an opening below the neck of the patient.

26. The system of claim 1, wherein the flange portion comprises at least one flat electrode.

27. The system of claim 26, wherein the at least one flat electrode is located on the bottom surface of the base.

28. The system of claim 1, wherein the protective cap is configured to frictionally engage the flange portion.

29. The system of claim 1, wherein the protective cap is configured to magnetically engage the flange portion.

30. The system of claim 1, wherein the protective cap is configured to engage two opposing sides of the base.

31. The system of claim 1, further comprising a wire bundle comprising: a proximal end and a distal end; and at least one filamentous insulated conductor; wherein the proximal end is attached to the base and the at least one filamentous conductor is electrically connected to the electrode.

32. The system of claim 31, wherein the wire bundle is surrounded by an outer covering.

33. The system of claim 32, wherein the outer covering comprises a flexible sheath.

34. The system of claim 32, wherein the outer covering comprises an elastomeric compound.

35. The system of claim 32, wherein the outer covering loosely surrounds the at least one filamentous conductor.

36. The system of claim 32, wherein the outer covering tightly surrounds the at least one filamentous conductor.

37. The system of claim 31, wherein the at least one filamentous insulated conductor comprises multiple filamentous conductors, and the multiple filamentous conductors are electrically connected to the electrodes.

38. The system of claim 31, wherein the protective cap is mechanically attached to a portion of the wire bundle.

39. The system of claim 31, wherein the wire bundle comprises a connector.

40. The system of claim 39, wherein the connector is configured to mate with a receptacle implanted under the skin of the patient.

41. The system of claim 31, wherein the distal end is attached to a transcutaneous pedestal connector.

42. The system of claim 41, wherein the transcutaneous pedestal connector comprises: a first portion located above the skin of the patient; a second portion located beneath the skin of the patient; an attachment member for securing the second portion under the skin of the patient; and at least one signal communication port configured to transport a signal to or from one or more electrodes.

43. The system of claim 31, wherein the distal end is attached to a second implant.

44. The system of claim 43, wherein the second implant comprises a signal processing circuitry for processing multicellular signals received from the multiple electrodes.

45. The system of claim 31, wherein at least a portion of the wire bundle is resiliently flexible.

46. The system of claim 45, wherein the wire bundle is resiliently flexible along a majority of its length.

47. The system of claim 31, wherein at least a portion of the wire bundle is plastically deformable.

48. The system of claim 47, wherein the wire bundle is plastically deformable along a majority of its length.

49. The system of claim 31, further comprising one or more templates for positioning the wire bundle.

50. The system of claim 49, wherein the one or more templates are capable of creating used to create a groove in the skull of the patient.

51. The system of claim 49, wherein the one or more templates provides instructions used by an operator to plastically deform the wire bundle into a shape.

52. The system of claim 51, wherein the wire bundle is plastically deformed by one or more of: bending; twisting; winding and stretching.

53. The system of claim 49, wherein the one or more templates are adjustable.

54. The system of claim 31, further comprising a winding tool for forming the wire bundle into one or more shapes.

55. The system of claim 54, further comprising a template for indicating the number of turns to wind the wire bundle.

56. The system of claim 54, wherein the winding tool is used to create one or more bends in the wire bundle.

57. The system of claim 54, wherein the winding tool comprises at least one of the projections about which the wire bundle is wound.

58. The system of claim 54, wherein the winding tool comprises multiple cylindrical projections.

59. The system of claim 1, further comprising an insertion tool for inserting the projections into tissue of the patient.

60. The system of claim 59, wherein the tissue comprises brain tissue.

61. The system of claim 59, wherein the tissue comprises peripheral nerve tissue.

62. The system of claim 59, wherein the insertion tool is configured to mechanically connect to the protective cap during insertion.

63. The system of claim 59, wherein the insertion tool is configured to be mechanically attached to the base of the sensor.

64. The system of claim 59, wherein the insertion tool is mechanically attached to the sensor during insertion.

65. The system of claim 1, wherein the flexible sheath is wire reinforced.

66. The system of claim 1, wherein the flexible sheath is configured to be implanted in the patient.

67. The system of claim 1, wherein the tunneling device is attached to the sensor utilizing one or more of: a magnet; a hook; a frictional engagement device; a Velcro; and any combination thereof.

68. The system of claim 1, wherein the tunneling device is attached to the sensor via one or more of: the base; the protective cap; a wire bundle attached to the sensor; or any combination thereof.

69. The system of claim 1, wherein the tunneling device has a detachable tip.

70. The system of claim 1, wherein the plurality of projections are arranged in a ten by ten array.

71. The system of claim 1, wherein the at least one electrode is configured to detect electric signals generated from neurons.

72. The system of claim 1, wherein the at least one electrode comprises at least one of a recording electrode, a stimulating electrode, and an electrode having recording and stimulating capabilities.

73. The system of claim 1, wherein the sensor comprises a set of electrodes arranged in an array.

74. The system of claim 1, wherein the sensor comprises multiple wires or wire bundle electrodes.

75. The system of claim 1, wherein the sensor comprises electrodes incorporated into one or more of: a subdural grid; a scalp electrode; a wire electrode; and a cuff electrode.

76. The system of claim 1, wherein the sensor comprises two or more discrete components.

77. The system of claim 76, wherein each of the discrete components comprises one or more electrodes.

78. The system of claim 76, wherein each of the discrete components comprises one or more of: a multi-electrode array; a wire or wire bundle; a subdural grid; and a scalp electrode.

79. The system of claim 1, wherein the at least one electrode is configured to detect multicellular signals for less than twenty-four hours.

80. The system of claim 1, wherein the at least one electrode chronically detects multicellular signals.

81. The system of claim 1, wherein the sensor further comprises a signal processing circuitry.

82. The system of claim 1, wherein the sensor is configured to detect multicellular signals and transmit the multicellular signals through a wireless connection.

83. The system of claim 82 wherein the sensor is capable of transmitting the multicellular signals wirelessly to a receiver mounted on the skull of the patient.

84. The system of claim 1, wherein the sensor further comprises a coil for power transmission to the sensor.

85. The system of claim 1, wherein the at least one electrode is capable of recording from clusters of neurons and outputting detected signals comprising multiple neuron signals.

86. The system of claim 85, wherein detected signals are a measure of the local field potential response from neural activity.

87. The system of claim 85, wherein the multiple neuron signals comprise one or more of: electrocorticogram signals, local field potentials, electroencephalogram signals, and peripheral nerve signals.

88. The system of claim 1, wherein the at least one electrode is capable of detecting a plurality of neuron signals.

89. The system of claim 1, wherein the system provides neural signal access.

90. The system of claim 1, wherein the patient is a human being.

91. The system of claim 1, wherein the patient is one or more of: a quadriplegic, a paraplegic, an amputee, a spinal chord injury victim, and a physically impaired person.

92. The system of claim 1, further comprising a processing unit configured to receive multicellular signals from the sensor, process the multicellular signals to produce a processed signal, and transmit the processed signal to a controlled device.

93. The system of claim 92, wherein the controlled device comprises a piece of medical equipment.

94. The system of claim 93, wherein the medical equipment is used to perform a surgical event.

95. The system of claim 92, wherein the controlled device is a communication device.

96. The system of claim 95, wherein the communication device transmits multiple pieces of information simultaneously.

97. The system of claim 92, wherein the controlled device is a piece of equipment with controllable moving parts.

98. The system of claim 97, wherein the equipment is one or more of: a watercraft, an aircraft; a land vehicle, and a reconnaissance robot.

99. The system of claim 92, wherein the processing unit comprises an integrated neuron spike sorting function.

100. The system of claim 99, wherein the neuron spike sorting function is configured to classify spikes with a minimum amplitude threshold.

101. The system of claim 92, wherein the processing unit comprises an element to amplify the multicellular signals.

102. The system of claim 101, wherein the multicellular signals are amplified by a gain of at least eighty.

103. The system of claim 92, wherein the processing unit utilizes neural net software routines to map neural signals into the processed signal to control the controlled device.

104. The system of claim 92, wherein the processing unit assigns one or more cellular signals to a specific use.

105. The system of claim 104, wherein the specific use is determined by the patient attempting an imagined movement or other imagined state.

106. The system of claim 92, wherein the processing unit utilizes one or more cellular signals that is under voluntary control of the patient.

107. The system of claim 92, wherein the processing unit utilizes two or more cellular signals that are mathematically combined to create the processed signal.

108. The system of claim 92, wherein the processing unit is configured to use a cellular signal from a neuron whose signal is separated from other nearby neurons.

109. The system of claim 92, wherein the processing unit is configured to convert an analog signal that represents a cellular signal to a digital signal.

110. The system of claim 92, further comprising a patient feedback module.

111. The system of claim 110, wherein the patient feedback module comprises one or more of: an audio transducer, a tactile transducer, a visual transducer, a video display, and an olfactory transducer.

112. The system of claim 110, wherein the patient feedback module comprises a stimulator, and a one or more neurons are stimulated to cause movement or sensation in a part of the patient's body.

113. The system of claim 92, further comprising a drug delivery system, wherein the processing unit transmits a signal to the drug delivery system to deliver a therapeutic agent or drug to at least a portion of the patient's body.

114. The system of claim 1, further comprising an embedded identifier.

115. The system of claim 114, wherein the embedded identifier is used to confirm compatibility of one or more discrete components of the system.

* * * * *